United States Patent [19]
Pegg et al.

[11] Patent Number: 5,739,157
[45] Date of Patent: Apr. 14, 1998

[54] DIASTEREOMERIC PURE TRIFLUOROMETHYL KETONE PEPTIDE DERIVATIVES AS INHIBITORS OF HUMAN LEUKOCYTE ELASTASE

[75] Inventors: Stephen John Pegg; George Joseph Sependa; Elwyn Peter Davies, all of Macclesfield, United Kingdom; Chris Allan Veale, Newark, Del.

[73] Assignee: Zeneca Limited, London, England

[21] Appl. No.: 682,526

[22] PCT Filed: Feb. 7, 1995

[86] PCT No.: PCT/GB95/00242

§ 371 Date: Jul. 25, 1996

§ 102(e) Date: Jul. 25, 1996

[87] PCT Pub. No.: WO95/21855

PCT Pub. Date: Aug. 17, 1995

[30] Foreign Application Priority Data

Feb. 11, 1994 [GB] United Kingdom ............ 9402680
Oct. 26, 1994 [GB] United Kingdom ............ 9421550

[51] Int. Cl.⁶ .................... A61K 31/165; A61K 31/40; C07D 207/09
[52] U.S. Cl. .................... 514/428; 548/566; 548/569; 548/570; 548/571; 548/574; 548/578
[58] Field of Search ................ 548/566, 569, 548/570, 571, 574, 578; 514/428

[56] References Cited

U.S. PATENT DOCUMENTS

| | | |
|---|---|---|
| 4,910,190 | 3/1990 | Bergeson et al. .................. 514/19 |
| 5,055,450 | 10/1991 | Edwards et al. ................... 514/19 |
| 5,194,588 | 3/1993 | Edwards et al. ................. 530/331 |
| 5,414,132 | 5/1995 | Stein et al. ...................... 564/503 |

FOREIGN PATENT DOCUMENTS

| | | |
|---|---|---|
| 189305 | 1/1986 | European Pat. Off. . |
| 276101 | 7/1988 | European Pat. Off. . |

OTHER PUBLICATIONS

Tetrahedron Lett. (1992), 33(30), 4279–82.

Tetrahedron: Asymmetry (1994), 5(2), 195–8.

J. Mol. Biol. (1988), 201(2), 423–8.

J. Medicinal Chemistry (1992) 35(4), 641–662.

*Primary Examiner*—Johann Richter
*Assistant Examiner*—Jane C. Osweicki
*Attorney, Agent, or Firm*—Liza D. Hohenschutz

[57] ABSTRACT

The present invention relates to pyrrolidine derivatives, and more particularly to the compound (S)-1-[(S)-2-(4-methoxybenzamido)-3-methylbutyryl]-N-[(S)-2-methyl-1-(trifluoroacetyl)propyl]pyrrolidine-2-carboxamide, shown by formula I, and solvates thereof. The present invention also provides pharmaceutical compositions, intermediates and methods of preparation of the compound. The compound of formula I is an inhibitor of human neutrophil elastase and is useful in the treatment of diseases in which the enzyme is implicated, such as, for example, emphysema and acute respiratory distress syndrome (ARDS).

16 Claims, 4 Drawing Sheets

DIASTEREOMERIC PURE TRIFLUOROMETHYL KETONE PEPTIDE DERIVATIVES AS INHIBITORS OF HUMAN LEUKOCYTE ELASTASE

This application is a 371 of PCT/GB95/00242 filed Feb. 7, 1995.

The present invention relates to pyrrolidine derivatives, and more particularly the compound (S)-1-[(S)-2-(4-methoxybenzamido)-3-methylbutyryl]-N-[(S)-2-methyl-1-(trifluoroacetyl)propyl]pyrrolidine-2-carboxamide, shown by the formula I (set out hereinafter)

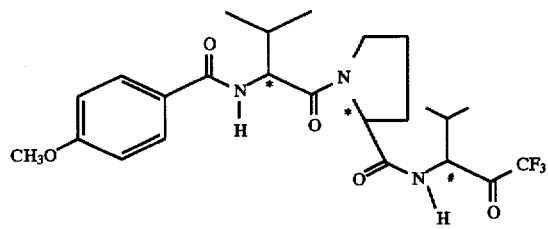

and having the S configuration at the chiral centres identified by the symbols * and #, and solvates thereof, which compound is an inhibitor of human leukocyte elastase (HLE), also known as human neutrophil elastase (HNE), which is of value, for example, as a research tool in pharmacological, diagnostic and related studies and in the treatment of diseases in mammals in which HLE is implicated. For example, HLE has been implicated causally in the pathogenesis of acute respiratory distress syndrome (ARDS), rheumatoid arthritis, atherosclerosis, pulmonary emphysema, and other inflammatory disorders, including airway inflammatory diseases characterized by increased and abnormal airway secretion such as acute and chronic bronchitis and cystic fibrosis. Also, HLE has been causally implicated in certain vascular diseases and related conditions (and their therapy) in which neutrophil participation is involved or implicated, for example, in hemorrhage associated with acute non-lymphocytic leukemia, as well as in reperfusion injury associated with, for example, myocardial ischaemia and related conditions associated with coronary artery disease such as angina and infarction, cerebrovascular ischaemia such as transient ischaemic attack and stroke, peripheral occlusive vascular disease such as intermittent claudication and critical limb ischaemia, venous insufficiency such as venous hypertension, varicose veins and venous ulceration, as well as impaired reperfusion states such as those associated with reconstructive vascular surgery, thrombolysis and angioplasty. The invention also concerns methods of treating one or more of these disease conditions and the use of the compound (or a solvate thereof) in the manufacture of a medicament for use in one or more of said conditions. The invention further concerns pharmaceutical compositions containing the compound, or a solvate thereof, as active ingredient, as well as processes for the manufacture of the compound (or a solvate thereof), novel intermediates useful in said processes and methods for the preparation of said intermediates.

Because of HLE's apparent role, there has been considerable research effort in recent years towards the development of HLE inhibitors. In U.S. Pat. No. 4,910,190 is disclosed a series of structurally related peptidoyl trifluoromethane derivatives which are HLE inhibitors. We have now discovered that the specific, pyrrolidine derivative named above is a potent inhibitor of HLE, possessing a surprising advantage in that it is a single diastereoisomer having a crystalline form. This provides a basis for the present invention. To use an HLE inhibitor which cannot be isolated in a crystalline form as, or in the formulation of, a medicament for treating the disease conditions referred to above, poses significant problems, for example, in the manufacture of the compound or formulation to the purity levels and uniformity required for regulatory approval. It is therefore highly desirable to find a novel crystalline HLE inhibitor and even more desirable to obtain a novel crystalline HLE inhibitor which is a single diastereoisomer. A further advantage of the compound of the invention is that it has been found to possess HLE inhibitory activity when administered orally. Prior to the present invention, the specific pyrrolidine derivative named above had not previously been prepared and therefore nothing was specifically known of its physical, chemical or pharmacological properties.

Figure 1:
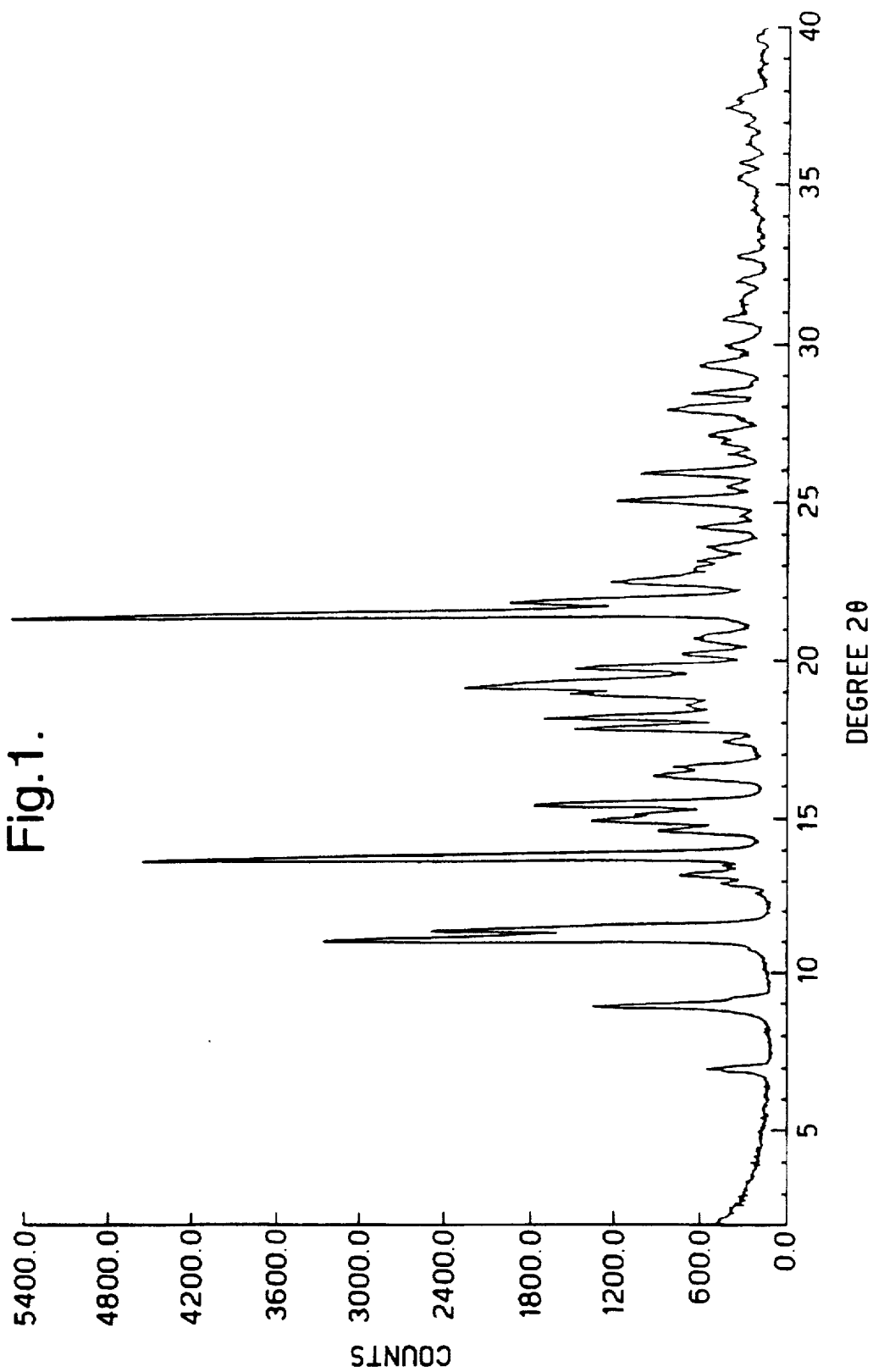
FIG. 1 shows an X-ray powder diffraction spectrum of a typical sample of the SSS diastereoisomer of formula I when it is substantially or essentially free of solvent.

According to the invention there is provided the compound (S)-1-[(S)-2-(4-methoxybenzamido)-3-methylbutyryl]-N-[(S)-2-methyl-1-(trifluoroacetyl)propyl]pyrrolidine-2-carboxamide, or a solvate thereof.

The compound of the invention, which may also be represented by the formula Ia

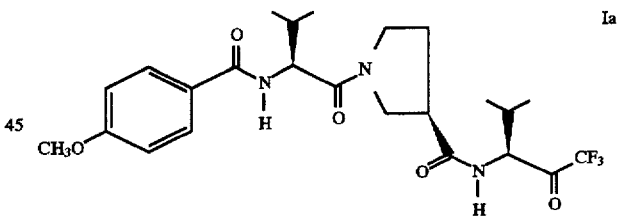

(in which a thickened line denotes a bond projecting in front of the plane of the paper) is a single diastereoisomer, hereinafter referred to as the "SSS diastereoisomer of formula I" or the "SSS diastereoisomer", to distinguish it from other possible diastereoisomers with different configurations at the chiral centres indicated by * and # in formula I, for example, the diastereoisomer which, in formula I, has the S configuration at the chiral centres marked * and the R configuration at the chiral centre marked # (hereinafter referred to as the "SSR diastereoisomer of formula I" or the "SSR diastereoisomer").

The SSS diastereoisomer of formula I is a crystalline solid, which exists in a form which is substantially or essentially free of solvent (hereinafter referred to as the "anhydrous" form), or as a solvated form. The solvated form may, for example, be a hydrated form, which may exist as a gem-diol of the trifluoroketone functionality, that is as a compound of the formula Ib

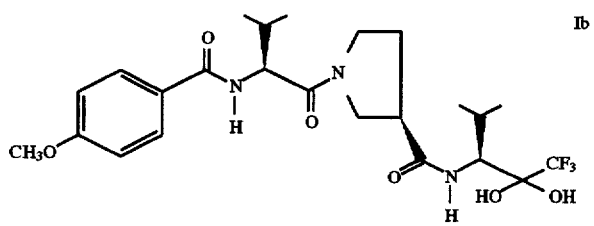

and/or a form which incorporates a water molecule as part of the crystal lattice. For example, the gem-diol Ib may itself be further hydrated. Crystalline SSS diastereoisomer may be obtained in which the ratio of anhydrous form to solvated (for example, hydrated) form is, for example, about 1:1 or greater, such as 4:1 or greater. When the compound of the invention is, for example, isolated substantially or essentially free of solvent, the ratio of anhydrous form to solvated (for example, hydrated) form is, for example, about 19:1 or better, that is 95% or more by weight of the compound is in the anhydrous form.

It will be appreciated that it is extremely difficult to obtain a compound which is a single diastereoisomer completely free of the other possible diastereomeric forms, particularly a compound which has three chiral centres. The present invention therefore includes a crystalline form of the SSS diastereoisomer of formula I, or solvate thereof, which contains other possible diastereoisomers with different configurations at the chiral centres indicated by * and # in formula I. It has been found that crystalline SSS diastereoisomer of formula I, or a solvate thereof, can be obtained which contains 25% or less of the SSR diastereoisomer of formula I, that is the crystalline material has a ratio of SSS:SSR forms of about 3:1 or more. The present invention therefore includes a crystalline form of the compound of formula I with a content of at least 75% of the SSS diastereoisomer. For example, crystalline material having a ratio of SSS:SSR of about 4:1 (or greater) and a ratio of anhydrous:hydrated forms of about 4:1 (or greater) can be obtained. Preferably, the crystalline SSS diastereoisomer of formula I, or a solvate thereof, is substantially or essentially pure, i.e. it contains less than 5% of one or more of the other possible diastereoisomers, for example, it contains less than 5% of the SSR diastereoisomer of formula I, preferably less than 3% of the SSR diastereoisomer of formula I, and more preferably less than 2% of the SSR diastereoisomer of formula I.

Preferably the SSS diastereoisomer of formula I is in the anhydrous form, i.e. substantially or essentially free of the solvated (for example, hydrated) form. In this form, the SSS diastereoisomer has the advantageous property that it is non-hygroscopic. It also possesses the advantageous property that in the solid state it has good epimeric stability. Thus a particularly preferred form of the SSS diastereoisomer of formula I is a form containing less than 2% of the SSR diastereoisomer of formula I and being 95% or more in the anhydrous form.

The melting point of the SSS diastereoisomer of formula I generally depends on the level of purity and may be determined by conventional procedures well known in the art, for example, by differential scanning calorimetry (DSC). Typically, the SSS diastereoisomer of formula I has a melting point which is in the range 147°–151° C., for example about 148°–150° C., in particular about 147°–149° C., when it is substantially or essentially in the anhydrous form and substantially or essentially free of the SSR diastereoisomer (heating rate 5° C./minute). However, when it exists as approximately a 1:1 mixture of anhydrous and hydrated forms, and is substantially or essentially free of the SSR diastereoisomer, it may be obtained in a form having typically a melting point of about 116°–117° C.

The SSS diastereoisomer of formula I, when it is substantially or essentially in the anhydrous form and substantially or essentially free of the SSR diastereoisomer, has an X-ray powder diffraction pattern including specific peaks at about 2Θ=8.95, 11.17, 11.47, 13.86, 15.49, 17.86, 18.22, 19.24, 21.58 and 21.92°.

The SSS diastereoisomer of formula I, when it exists as substantially a 1:1 mixture of anhydrous and hydrated forms having melting point about 116°–117° C., has an X-ray powder diffraction pattern including specific peaks at about 2Θ=6.20, 9.81, 10.29, 12.33, 12.44, 14.22 and 17.92°.

Additionally, the SSS diastereoisomer of formula I may be obtained in a crystalline hydrated form which is substantially or essentially free of the SSR diastereoisomer and which by differential scanning calorimetry (heating rate 2° C./minute) has an endothermic event with onset at about 91°–92° C. (with a peak at about 99°–100° C.), followed by an exothermic event with onset at about 109°–110° C. (with a peak at about 111°–112° C.), followed by a further endothermic event with onset at about 148°–149° C. (with a peak value at about 150°–151° C.). This hydrated form has an X-ray powder diffraction pattern including specific peaks at about 2Θ=6.62, 10.43, 13.30, 16.17, 19.51, 21.37 and 22.80°. The DSC data, together with thermogravimetric analysis (TGA) data and $^{19}F$ NMR spectral data, indicate that this form is substantially the monohydrate of the gem-diol (of formula Ib). It will be appreciated that the onset and peak values quoted above may vary slightly in accordance with the scanning speed employed. For example, a similar DSC scan carried out at a scanning speed of 5° C./minute showed onset of the first endothermic event at about 95°–96° C. (with a peak at 105°–106° C.).

The X-ray powder diffraction spectra were determined using Scintag XDS-2000 X-ray diffractometer, with an EC&G solid-state photon detector, GLP Series (germanium) operated by a Microvax computer and using the Diffraction Management System software supplied by Scintag Inc., Sunnydale, Calif., USA. The X-ray tube used was a Cu K-alpha with a wavelength of 1.5406A at 45 KV and 40 mA. The receiving slits were set at 2 and 4 mm and the diverging slits set at 0.5 and 0.2 mm with respect to the path of the incident beam. The spectra were obtained in the continuous scan mode with a chopper increment of 0.02. Each sample was exposed at 1 degree 2-theta per minute (running time was 38 minutes) and collected from 2 to 40 degrees 2-theta, to produce a trace of spacings against intensity for this range.

For diffraction analysis the samples were packed into round aluminium alloy sample pans with a diameter of 25 mm and depth of 2 mm. The powder sample was placed in the pan so that an amount in excess of the pan volume was present and subsequently leveled to the pan rim with a glass microscope slide. Silicon type-NBS 640b was used as an external standard.

Figure 2:
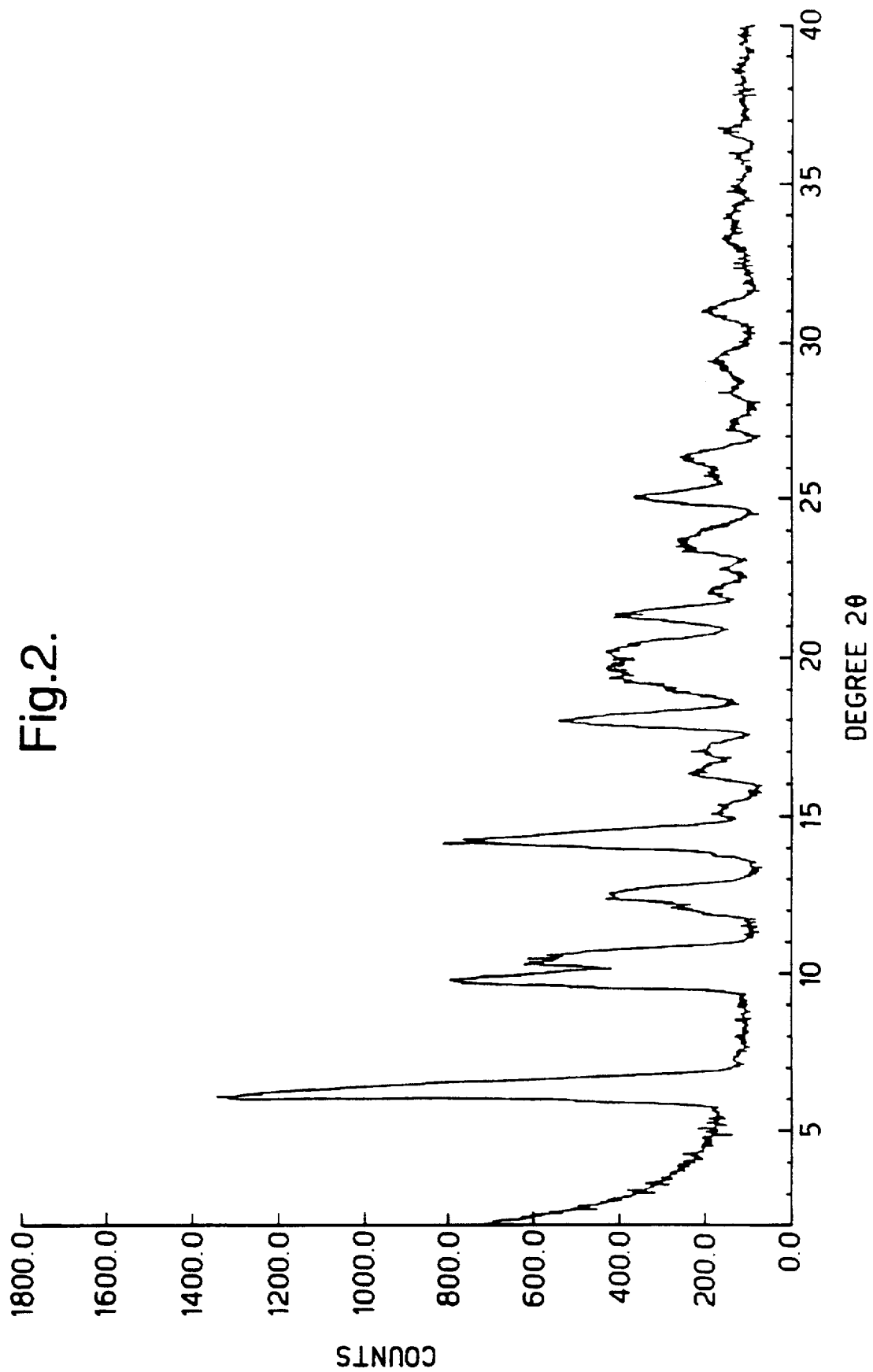
FIG. 2 shows an X-ray powder diffraction spectrum of a typical sample of the SSS diastereoisomer of the formula I when it is approximately a 1:1 mixture of anhydrous and hydrated forms.
Figure 3:
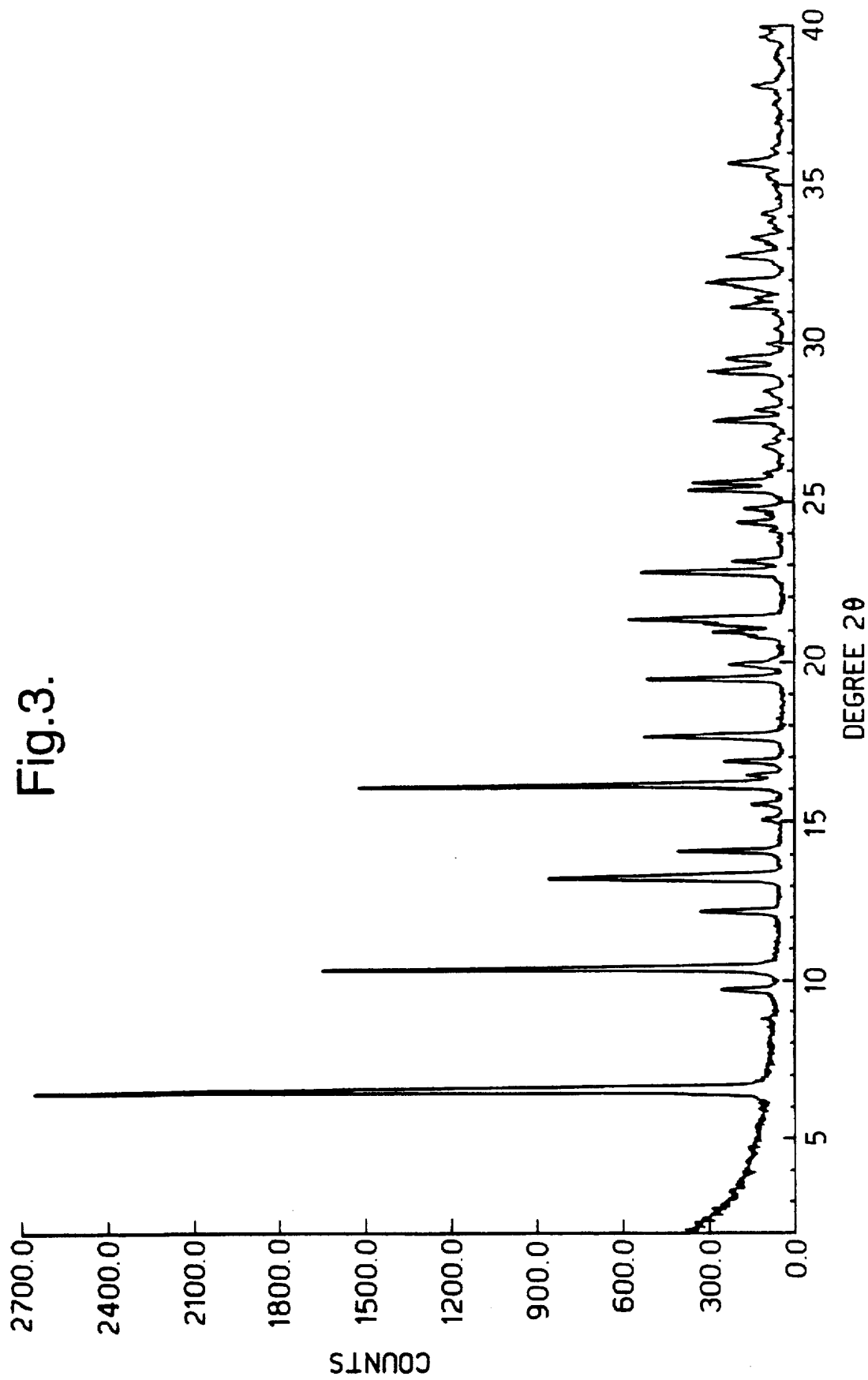
FIG. 3 shows an X-ray powder diffraction spectrum of a typical sample of the SSS diastereoisomer of the formula I when it is in a hydrated (gem-diol monohydrate) form.

X-ray powder diffraction spectra of typical samples of the SSS diastereoisomer of the formula I when it is substantially or essentially free of solvent, when it is approximately a 1:1 mixture of anhydrous and hydrated forms and when it is in a hydrated (gem-diol monohydrate) form are shown in FIGS. 1, 2 and 3 respectively hereinafter.

Infra-red spectra were obtained for typical samples of the SSS diastereoisomer of the formula I when it is substantially or essentially free of solvent, when it is approximately a 1:1 mixture of anhydrous and hydrated forms, and when it is the monohydrate of formula Ib. The infra-red spectra were obtained by the solvent cast technique well known in the art, from acetonitrile castings of a sample onto a salt (e.g. ZnSe or KBr) window for analysis by direct transmission. The infra-red spectra were determined over the wave number range 4000 to 400 cm$^{-1}$.

Figure 4:
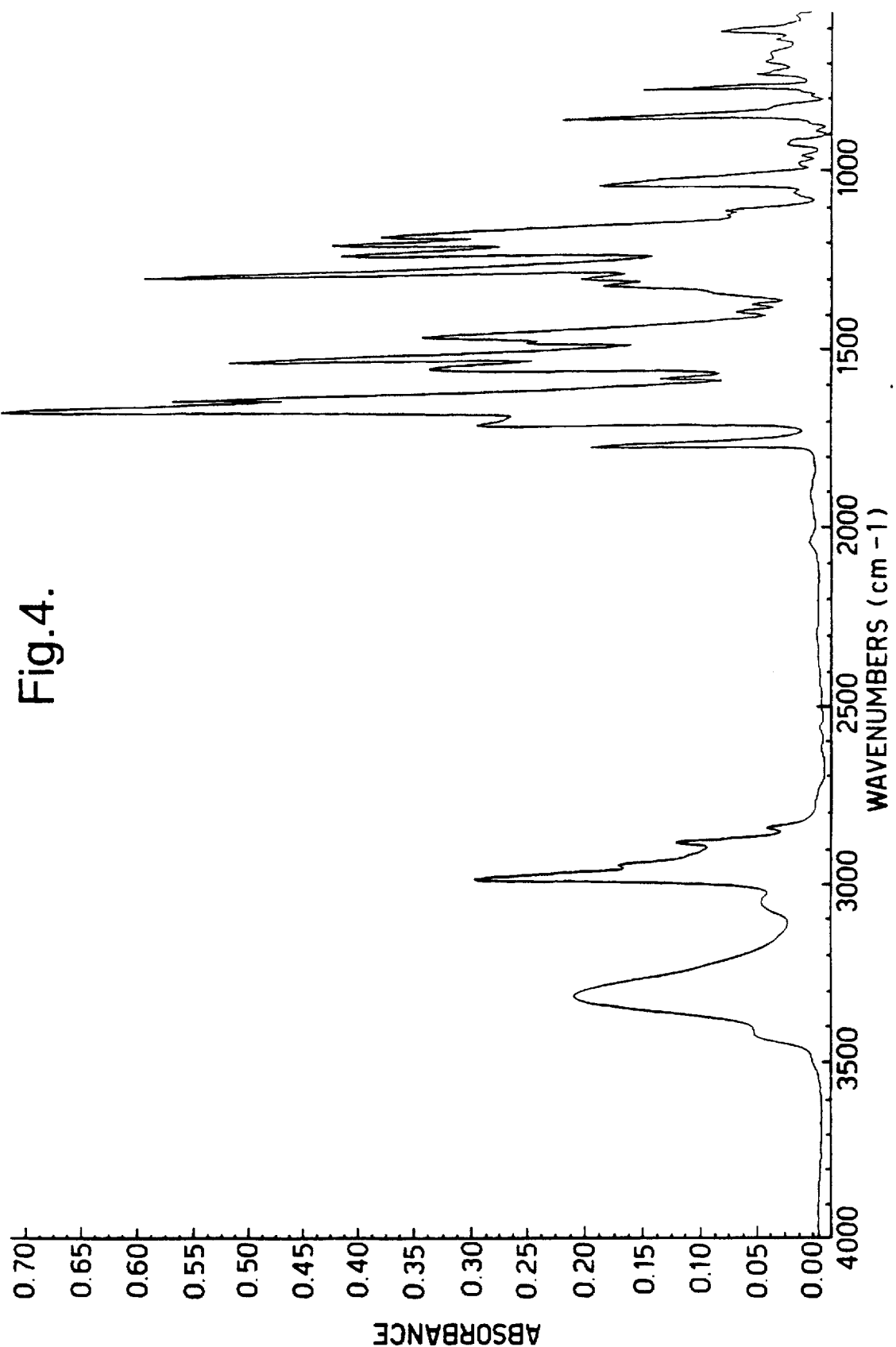
FIG. 4 shows the infra red-spectrum of a sample of the SSS diastereoisomer of the formula I when it is substantially or essentially free of solvent.

The infra red-spectrum of a sample of the SSS diastereoisomer of the formula I when it is substantially or essentially free of solvent is shown in FIG. 4. The spectrum of FIG. 4 includes sharp peaks at about 2968, 1761, 1629, 1607, 1533, 1503, 1443, 1259, 1209, 1178, 1158, 1032, 845 and 767 cm$^{-1}$. The infra-red spectrum of a sample of the SSS diastereoisomer of the formula I when it is approximately a 1:1 mixture of anhydrous and hydrated forms, and that of a sample of the monohydrate of the gem-diol of formula Ib, were not significantly different to that of FIG. 3 due to the nature of the solvent cast technique and the solvent employed.

It will be understood that the 2θ values of the X-ray powder diffraction patterns and the wavelengths of the infra-red spectra may vary slightly from one machine to another and so the values quoted are not to be construed as absolute.

It will be appreciated that the hydrogen atoms of the hydroxyl groups of the gem-diol of formula Ib are acidic and that such compounds may therefore form crystalline pharmaceutically-acceptable salts, using conventional procedures, for example with bases affording physiologically-acceptable cations, for example alkali metal (such as sodium or potassium), alkali earth metal or organic amine salts. The invention therefore includes crystalline pharmaceutically-acceptable salts of a gem-diol of formula Ib or a hydrate thereof.

The SSS diastereoisomer of formula I, or solvates thereof, may be obtained, by the following processes, which are further separate aspects of the invention.

Crystalline SSS diastereoisomer containing less than 25% SSR diastereoisomers may be obtained from a non-crystalline (amorphous) diastereomeric mixture of the SSS and SSR diastereoisomers, containing the SSS and SSR diastereoisomers in approximately equal amounts (i.e. a ratio of about 1:1 to about 3:2 SSS:SSR), by crystallisation from a suitable non-polar solvent, such as diethyl ether, di-n-propyl ether or di-n-butyl ether, or a mixture of solvents, such as a mixture of methyl tert-butyl ether and hexane or, preferably, a mixture of ethyl acetate and hexane. To initiate crystallisation, seeding with crystalline SSS diastereoisomer is required. One preferred such crystallisation process comprises reducing the volume of the solution of a non-crystalline diastereomeric mixture of the SSS and SSR diastereoisomers in ethyl acetate by evaporation or distillation, adding hexane to the hot solution and maintaining a clear solution, seeding with substantially pure SSS diastereoisomer and allowing to cool gradually. A modification of this process includes the use of a solution of the non-crystalline diastereomeric mixture of the SSS and SSR diastereoisomers in a lower boiling solvent to that of ethyl acetate (such as methyl tert-butyl ether), for example as may be obtained directly from the work-up of the preparation of the non-crystalline mixture (as discussed below) and swapping the solvent for ethyl acetate by adding ethyl acetate and concentrating the solution by evaporation or distillation at atmospheric pressure, prior to the addition of the hexane.

Dependent on the solvent employed and the precise conditions used for the crystallisation, the product may be initially isolated as a mixture of anhydrous and hydrated diastereoisomers, for example, having a ratio of anhydrous:hydrated forms of about 1:1 or greater. Crystalline product having a ratio of anhydrous:hydrated forms of about 4:1 may, for example, be obtained.

Substantially or essentially pure crystalline SSS diastereoisomer of formula I, substantially or essentially in the anhydrous form, for example, containing about 5% or less of the hydrated form, may be obtained by repeated recrystallisation of crystalline SSS diastereoisomer containing SSR diastereoisomer. A non-polar solvent which forms an azeotrope with water is generally employed for this purpose. This facilitates the removal of water from the system when the SSS diastereoisomer of formula I, containing SSR diastereoisomer, is dissolved by heating or boiling in a solvent of crystallisation, preferably with concentration of the solution, prior to addition of a second solvent if required, and allowing crystallisation to take place. Toluene is a particularly suitable solvent for this purpose, or a mixture of ethyl acetate and hexane in which the hexane is added after azeotropic removal of water from the ethyl acetate solution. Crystalline SSS diastereoisomer which is substantially or essentially pure and substantially or essentially in the anhydrous form may subsequently also be recrystallised from alternative solvents, including n-butyl acetate, isopropyl acetate, 1,2-dimethoxyethane, 2,2-dimethoxypropane, tert-butanol, tert-amyl methyl ether and mixtures of dichloromethane and hexane, methyl ethyl ketone and hexane, N,N-dimethylformamide and methyl tert-butyl ether, dipropyl ether and acetonitrile, 1,4-dioxane and hexane, methyl ethyl ketone and isohexane, tetrahydrofuran and cyclohexane, ethyl acetate and isohexane, tetrahydrofuran and hexane, tetrahydrofuran and isohexane, diethyl ether and ethyl acetate, and tert-amyl methyl ether and acetonitrile. A single crystallisation from any of the above solvents may be sufficient to obtain SSS diastereoisomer containing 5% or less of SSR diastereoisomer. In all recrystallisations, initiation of crystallisation by seeding is preferred.

Alternatively, a substantially or essentially pure hydrated form (which data indicates to be a gem-diol monohydrate) may be obtained by repeated recrystallisation of crystalline SSS diastereoisomer containing SSR diastereoisomer using a mixture of acetone and water or a mixture of tert-butanol and water as solvent.

When carrying out the crystallisations or recrystallisations referred to above, preferably the ratio of volume of solvent (in ml) to weight of SSS diastereoisomer containing SSR diastereoisomer (in grams) is, for example, in the range of 2:1 to 15:1, and conveniently about 6:1 to 10:1.

A non-crystalline (amorphous) diastereomeric mixture of SSS and SSR diastereoisomers as referred to above may be obtained as described in Example 20 of U.S. Pat. No. 4,910,190 or by the analogous process illustrated in Scheme 1.

Alternatively the novel process illustrated in Scheme 2 may be used, in which the novel intermediate N-(4-methoxybenzoyl)-L-valyl-L-proline (or a salt thereof), which is a further aspect of the invention, is coupled with 3-amino-4-methyl-1,1,1-trifluoro-2-pentanol, followed by conventional oxidation of the alcohol product to the corresponding ketone. Conventional procedures for similar coupling and oxidation reactions are described herein and in U.S. Pat. No. 4,910,190. An advantage of this process is that it allows incorporation of the aminoalcohol at a later stage. The novel intermediate may be obtained using the conventional steps of selective deprotection, coupling and deprotection (Scheme 2, steps (a)–(c)), as illustrated in Procedure 1 hereinafter. Alternatively, N-tert-butyloxycarbonylvaline is coupled with the proline benzyl ester, for example, using N-hydroxybenztriazole and dicyclohexylcarbodiimide in dichloromethane at 0° C., followed by removal of the tert-butyloxycarbonyl protecting group using trifluoroacetic acid to give L-valyl-L-proline benzyl ester. This is then coupled with, for example, anisoyl chloride in dichloromethane at about ambient temperature in the presence of triethylamine, and the benzyl protecting group is then removed by hydrogenolysis. The diastereomeric mixture obtained using these processes has an SSS:SSR ratio of about 1:1 to 3:2 and has only been isolated in a non-crystalline form, such as a foam or oil.

Alternatively, a particularly advantageous process for the manufacture of the novel intermediate N-(4-methoxybenzoyl)-L-valyl-L-proline, which is another aspect of the present invention, is characterised by the following steps:

(i) reaction of L-valyl-L-proline (or a salt thereof) with a tri(1–4C)alkylhalogenosilane, (for example, trimethylchlorosilane) or bis(tri(1–4C)alkylsilyl) acetamide (such as bis(trimethylsilyl)acetamide) to give L-valyl-L-proline tri(1–4C)alkylsilyl ester (for example L-valyl-L-proline trimethylsilyl ester); followed by (ii) reaction of the L-valyl-L-proline tri(1–4C)alkylsilyl ester with an activated derivative of 4-methoxybenzoic acid (for example, an acid chloride such as 4-methoxybenzoyl chloride (also known as anisoyl chloride) or an anhydride), to give N-(4-methoxybenzoyl)-L-valyl-L-proline tri(1–4C) alkylsilyl ester; followed by (iii) removal of the tri(1–4C)alkylsilyl protecting group Step (i) is conveniently carried out in a suitable inert solvent or diluent, for example ethyl acetate, an ethereal solvent or diluent (such as tetrahydrofuran or dioxan) or a hydrocarbon solvent such as toluene, in the presence of an organic base such as, for example, triethylamine, pyridine or, preferably, N-methylmorpholine, or an inorganic base such as sodium or potassium carbonate. The reaction is carried out at a temperature in the range, for example, from –10° to 50° C., and preferably between 0° to 30° C. Preferably about two equivalents of base are used per equivalent of L-valyl-L-proline (or 3 equivalents of base are employed if a salt, such as L-valyl-L-proline hydrochloride, is used). Preferably about 2 equivalents or more of the silylating agent are used per equivalent of L-valyl-L-proline.

Step (ii) is carried out under anhydrous conditions using a conventional method. For example, 4-methoxybenzoyl chloride is used and similar conditions to step (i) are employed. In this case, about one equivalent of acid chloride to one equivalent of base (or a slight excess) are used. Preferably the product of step (i) is not isolated, but is reacted in situ by addition of a further equivalent of the same base as used in step (i), followed by one equivalent of the acid chloride.

Step (iii) is carried out using a conventional procedure for the deprotection of a silyl protecting group, for example by hydrolysis under aqueous conditions. Conveniently the silyl protecting group is removed during the work-up procedure of step (ii). It will be appreciated that other conventional silylating agents may be used in step (i) to form the corresponding silyl ester of L-valyl-L-proline, which may then be used in step (ii) and the silyl protecting group then removed as in step (iii).

To obtain a non-crystalline (amorphous) diastereomeric mixture of SSS and SSR diastereoisomers, for use as starting material to prepare the compound of the invention, steps (i)–(iii) may be followed by:

(iv) reaction of N-(4-methoxybenzoyl)-L-valyl-L-proline with 3-amino-4-methyl-1,1,1-trifluoro-2-pentanol to give (S)-1-[(S)-2-(4-methoxybenzamido)-3-methylbutyryl]-N-[2-methyl-1-(2,2,2-trifluoro-1-hydroxyethyl)propyl]pyrrolidine-2-carboxamide; followed by (v) oxidation of (S)-1-[(S)-2-(4-methoxybenzamido)-3-methylbutyryl]-N-[2-methyl-1-(2,2,2-trifluoro-1-hydroxyethyl)propyl]pyrrolidine-2-carboxamide, corresponding to steps (d) and (e) in Scheme 2.

Step (iv) is carried out using a conventional method for coupling a carboxylic acid to an amine to form an amide linkage, such as those described in U.S. Pat. No. 4,910,190. Particularly suitable is the use of a chloroformate, for example an alkyl chloroformate (such as isobutyl chloroformate) in the presence of a tertiary amine (such as triethylamine or, preferable N-methylmorpholine), in a suitable solvent or diluent, for example a chlorinated solvent or diluent such as dichloromethane, an ethereal solvent or diluent such as tetrahydrofuran or methyl tert-butyl ether, or a hydrocarbon solvent or diluent such as toluene. A mixture of solvents or diluents may be used, for example a mixture of toluene and tetrahydrofuran. The reaction is generally carried out at a temperature in the range, for example, –15° C. to 30° C. and preferably between –10° C. to 20° C. A reverse addition of the preformed mixed anhydride to a slurry of the aminoalcohol, for example using methyl tert-butyl ether as solvent, may also be used.

Step (v) is carried out using a conventional oxidising agent for the conversion of a hydroxy group into a ketone group. Suitable oxidising agents and conditions include, for example, the use of oxalyl chloride, dimethyl sulfoxide, and a tertiary amine; the use of acetic anhydride and dimethyl sulfoxide; the use of chromium trioxide pyridine complex in dichloromethane; the use of hypervalent iodine reagent, such as 1,1,1-triacetoxy-2,1-benzoxidol-3(3H)-one with trifluoroacetic acid in dichloromethane; the use of excess dimethylsulphoxide and a water soluble carbodiimide in the presence of dichloroacetic acid; or alkaline aqueous potassium permanganate solution. Particularly suitable oxidising agents are the latter two named, especially alkaline aqueous potassium permanganate solution, for example a mixture of sodium hydroxide and potassium permanganate.

3-Amino-4-methyl-1,1,1-trifluoro-2-pentanol may be obtained as described in U.S. Pat. No. 4,910,190 or as illustrated in the Examples.

Alternatively, if (S)-1-[(S)-2-(4-methoxybenzamido)-3-methylbutyryl]-N-[(S)-2-methyl-1-((R)-2,2,2-trifluoro-1-hydroxyethyl)propyl]pyrrolidine-2-carboxamide (which may be obtained, for example, using analogous procedures to those shown in Scheme 1 or 2, but using the resolved aminoalcohol 2(R),3(S)-3-amino-4-methyl-1,1,1-trifluoro-2-pentanol, itself obtained as described in U.S. Pat. No. 4,910,190 or as described in the Examples hereinafter) is oxidised, then the amorphous material isolated may be crystallised to provide substantially or essentially pure crystalline SSS diastereoisomer as a mixture of anhydrous and hydrated forms (for example, if diethyl ether is used as solvent of crystallisation), or substantially the anhydrous form (for example, if the material is crystallised or recrystallised from toluene).

The oxidation may be carried out using analogous conditions to those described in step (v) above.

A particularly advantageous procedure for the manufacture of the SSS diastereoisomer of formula I, which is a still further aspect of the present invention, is characterised by heating a non-crystalline (amorphous) diastereomeric mixture of SSS and SSR diastereoisomers of formula I with a suitable base, for example a tertiary base such as an N-(1–4C)alkylmorpholine (for example, N-methylmorpholine), an N-(1–4C)alkylpiperidine (for example N-ethylpiperidine), pyridine or pentaisopropylguanidine, in a suitable non-polar solvent or diluent, for example, methyl tert-butyl ether, hexane or, preferably, a mixture of hydrocarbons having a boiling point in the range 100°–120° C. (for example a petroleum fraction, b.p. 100°–120° C. such as 'ESSOCHEM 30' (a trademark)), or mixtures thereof, or a mixture of ethyl acetate and hexane. As the solution is allowed to cool gradually, SSS diastereoisomer crystallises from the solution and epimerisation of the then SSR-enriched diastereomeric mixture remaining in the hot or warm solution takes place, whereby further SSS diastereoisomer is produced which crystallises. Thus the equilibrium is driven in favour of the SSS-diastereoisomer. This epimerisation/crystallisation process therefore allows conversion of SSR diastereoisomer into SSS diastereoisomer, or recycling of mother liquors enriched in the SSR diastereoisomer, to produce further amounts of SSS diastereoisomer. The process therefore has an advantage that it may be carried out using either an SSS- or SSR-enriched diastereomeric mixture. A preferred base for use in the epimerisation/crystallisation process is N-methylmorpholine.

Dependent on the solvent or diluent employed, the heating is generally carried out, for example, at a temperature in the range of 50°–130° C., and conveniently, for example, initially at the refluxing temperature of the solvent or diluent, prior to allowing the reaction mixture to cool gradually and crystallisation of the SSS diastereoisomer to take place. It is preferable that the reaction mixture is heated so that distillation of solvent occurs, prior to cooling. A miscible non-polar solvent or diluent in which the SSS diastereoisomer is less soluble may be added to the heated solution to aid crystallisation. This addition may conveniently be carried out while distillation of the initial solvent or diluent is taking place, to prevent premature crystallisation of product. Alternatively, the initial solvent in which the diastereomeric mixture and base are heated may be substantially replaced by a miscible non-polar solvent of higher boiling point in which the SSS diastereoisomer is less soluble, prior to gradual cooling. For example, when methyl tert-butyl ether is used as solvent, a mixture of hydrocarbons having a boiling point in the range 100°–120° C. may be added (for example a petroleum fraction, b.p. 100–120, such as ESSOCHEM 30), optionally with the addition of one or more other such solvents, such as toluene, with simultaneous removal of the lower boiling solvent by distillation, prior to cooling. It will be appreciated that this modification allows a diastereomeric mixture which is initially isolated as a solution in a substantially non-polar solvent to be used directly to obtain crystalline SSS diastereoisomer.

To initiate crystallisation, seeding with crystalline SSS diastereoisomer is required. Preferably crystallisation is carried out by allowing the temperature of the mixture to cool slowly to ambient temperature, for example by allowing the temperature to fall in 10° C. steps and maintaining at each temperature for about one hour. Preferably 0.5–1 equivalent of base per equivalent of amorphous starting material is used, especially about 1 equivalent.

A modification of this epimerisation/crystallisation process which may be used to prepare the SSS diastereoisomer of formula I is crystallisation of a non-crystalline mixture of the SSS and SSR diastereoisomers from a suitable non-polar solvent (as referred to above), such as a mixture of ethyl acetate and hexane, in the presence of a catalytic amount (for example about 10 mole %) of a base (as defined above), for example N-methylmorpholine.

Using the epimerisation/crystallisation process, the crystalline material initially isolated is crystalline SSS diastereoisomer containing less than 25% SSR diastereoisomer, for example crystalline material with a ratio of SSS:SSR of 4:1 or better is generally obtained. The material is generally initially isolated as a mixture of anhydrous and hydrated forms. Substantially or essentially pure crystalline SSS diastereoisomer of formula I, substantially or essentially in the anhydrous form, for example, containing about 5% or less of the hydrated form, or a crystalline hydrated form, may be obtained by recrystallisation of this material as described hereinbefore.

It is preferable to remove any residual base from the product isolated from the epimerisation/crystallisation process prior to further purification by recrystallisation, to avoid epimerisation of the product back to a diastereomeric mixture. This is achieved, for example, by washing the isolated product with dilute aqueous acid, for example dilute hydrochloric acid or dilute sulphuric acid.

The utility of the compound of the invention may be demonstrated by standard tests and clinical studies, including those described below.

Inhibition Measurements

The potency of the compound of the invention to act as an inhibitor of human leukocyte elastase (HLE) on the low molecular weight peptide substrate methoxy-succinyl-alanyl-alanyl-prolyl-valine-p-nitroanilide is determined as described in U.S. Pat. No. 4,910,190. The potency of the compound is evaluated by obtaining a kinetic determination of the dissociation constant, $K_i$, of the complex formed from the interaction of the inhibitor with HLE. The compound of the invention was found to have a Ki of 6.7 nM.

Acute Lung Injury Model

Animal models of emphysema include intratracheal (i.t.) administration of an elastolytic protease to cause a slowly progressive, destructive lesion of the lung. These lesions are normally evaluated a few weeks to a few months after the initial insult. However, these proteases also induce a lesion that is evident in the first few hours. The early lesion is first hemorrhagic, progresses to an inflammatory lesion by the end of the first 24 hours and resolves in the first week post insult. To take advantage of this early lesion, the following model may be used.

Hamsters are first lightly anesthetized with Brevital. Phosphate buffered saline (PBS) pH 7.4, either alone or containing human leukocyte elastase (HLE), is then administered directly into the trachea. Twenty-four hours later the animals are killed and the lungs removed and carefully trimmed of extraneous tissue. Following determination of wet lung weight, the lungs are lavaged with PBS and total lavagable red and white cells recovered are determined. The values for wet lung weights, total lavagable red cells and total lavagable white cells are elevated in a dose-dependent manner following administration of HLE. Compounds that are effective elastase inhibitors can prevent or diminish the severity of the enzyme-induced lesion resulting in lower wet lung weight and reduced values for total lavagable cells, both red and white, relative to administration of HLE alone. Compounds can be evaluated by administering them intratracheally as solutions or suspensions in PBS, either with or at various times prior to the HLE challenge (400 µg), or by dosing them intravenously or orally as solutions at various times prior to the HLE challenge (100 µg) to determine their utility in preventing an HLE lesion. A solution of the compound of the invention is conveniently prepared using 10% polyethylene glycol 400/PBS.

Acute Hemorrhagic Assay

This assay relies on monitoring only the amount of hemorrhage in the lung following intratracheal administration of human neutrophil elastase (HNE). Hemorrhage is quantified by disrupting erythrocytes recovered in lung lavage fluid and comparing that to dilutions of whole hamster blood. The screening protocol, similar to that described in Fletcher et al., *American Review of Respiratory Disease* (1990), 141, 672–677, is as follows. Compounds demonstrated to be HNE inhibitors in vitro are conveniently prepared for dosing as described above for the Acute Lung Injury Model. Male Syrian hamsters (fasted for 16–18 hours prior to use) are lightly anaesthetised with Brevital sodium (30 mg/kg i.p.). The compounds are then dosed intravenously or orally to the hamsters at a fixed time, such as 30 or 90 min, prior to intratracheal administration of 50 µg/animal of HNE in 300 µL phosphate buffered saline (PBS) pH 7.4. Four hours after enzyme administration, the animals are killed with an overdose of pentobarbital sodium, the thorax opened and the lungs and heart removed and the lungs cleared of extraneous material. The excised lungs are lavaged with three changes of 2 ml PBS via a tracheal cannula. The recovered lavages are pooled, the volumes (about 5 mL) are recorded and the lavages stored at 4° C. until assayed. For calculation of the amount of blood in each sample, the thawed lavages and a sample of whole hamster blood are sonicated to disrupt erythrocytes and appropriately diluted into individual wells of a 96-well microtiter plate. The optical densities (OD) of the disrupted lavages and blood samples are determined at 540 nm. The (µL blood equivalents)/(mL lavage) are determined by comparing the OD of the test samples with the OD of the standard curve prepared from whole hamster blood. The total µL equivalents of blood recovered is determined by multiplying recovered lavage volume by the (µL blood equivalents)/(mL lavage) for each sample. Results are reported as % inhibition of HNE-induced hemorrhage with respect to PBS treated controls when the test compound is given at a specified dose and time prior to administration of HNE. The $ED_{50}$ for the compound of the invention was found to be 5.2 mg/kg after oral dosing and 0.59 mg/kg after i.v. administration.

No overt toxicity was observed when the compound of the invention was administered in the above in vivo tests.

It will be appreciated that the implications of a compound's activity in the Acute Lung Injury Model or Acute Hemorrhagic Assay are not limited to emphysema, but, rather, that the test provides evidence of general in vivo inhibition of HLE.

According to a further feature of the invention, there is provided a pharmaceutical composition comprising a pharmaceutically effective amount of the compound of the invention, or a solvate thereof, and a pharmaceutically acceptable diluent or carrier. As noted above, another feature of the invention is a method of using the compound of the invention, or a solvate thereof, in the treatment of a disease or condition in a mammal, especially a human, in which HLE is implicated, such as those referred to hereinbefore, and particularly acute and chronic bronchitis, pulmonary emphysema, reperfusion injury, adult respiratory distress syndrome, cystic fibrosis, or peripheral vascular disease (such as critical limb ischaemia or intermittent claudication).

The compound of the present invention may be administered to a warm-blooded animal, particularly a human, in need thereof for treatment of a disease in which HLE is implicated, in the form of a conventional pharmaceutical composition, for example as generally disclosed in U.S. Pat. No. 4,910,190. One mode of administration may be via a powdered or liquid aerosol. In a powdered aerosol, the compound of the invention may be administered in the same manner as cromolyn sodium via a 'Spinhaler' (a trademark) turbo-inhaler device obtained from Fisons Corp. of Bedford, Mass. at a rate of about 0.1 to 50 mg per capsule, 1 to 8 capsules being administered daily for an average human. Each capsule to be used in the turbo-inhaler contains the required amount of the compound of the invention with the remainder of the 20 mg capsule being a pharmaceutically acceptable carrier such as lactose. In a liquid aerosol, the compound of the invention may be administered using a nebulizer such as, for example, a 'Retec' (trademark) nebulizer, in which the solution is nebulized with compressed air. The aerosol may be administered, for example, at the rate of one to about eight times per day as follows: A nebulizer is filled with a solution of the compound, for example 3.5 mL of solution containing 10 mg/mL; the solution in the nebulizer is nebulized with compressed air; and the patient breathes normally (tidal volume) for eight minutes with the nebulizer in his mouth.

Alternatively, the mode of adminstration may be parenteral, including subcutaneous deposit by means of an osmotic pump or, preferably, oral. The compound of the invention may be conventionally formulated in an oral or parenteral dosage form by compounding about 10 to 250 mg per unit of dosage with conventional vehicle, excipient, binder, preservative, stabilizer, flavor or the like as called for by accepted pharmaceutical practice, e.g. as described in U.S. Pat. No. 3,755,340. For parenteral administration, a 1 to 10 mL intravenous, intramuscular or subcutaneous injection would be given containing about 0.02 mg to 10 mg/kg of body weight of the compound of the invention 3 or 4 times daily. The injection would contain the compound of the invention in an aqueous isotonic sterile solution or suspension optionally with a preservative such as phenol or a solubilizing agent such as ethylenediaminetetraacetic acid (EDTA). For parenteral administration or use in an aerosol, an aqueous formulation may be prepared, for example, by dissolving the compound in 5–10% polyethylene glycol 400/phosphate buffered saline, followed by aseptic filtration, and sterile storage using standard procedures.

In general, the compound of the invention will be administered to humans at a daily dose in the range of, for example, 5 to 100 mg of the compound by aerosol or 50 to 1000 mg intravenously or orally, or a combination thereof. However, it readily will be understood that it may be necessary to vary the dose of the compound adminstered in accordance with well known medical practice to take account of the nature and severity of the disease under treatment, concurrent therapy, and the age, weight and sex of the patient receiving treatment. It similarly will be understood that generally equivalent amounts of a solvated (for example, hydrated) form of the compound also may be used. Protocols for the administration of an HLE inhibitor and evaluation of the patients are described in the European Patent Applications with Publication Numbers 458535, 458536, 458537, and 463811 for the treatment or prevention of cystic fibrosis, ARDS, bronchitis, and hemorrhage associated with acute non-lymphocytic leukemia or its therapy, respectively; and the compound of the invention may be used similarly, or preferably used by oral administration, for the treatment of those diseases and conditions either alone or in combination with another therapeutic agent customarily indicated for the treatment of the particular condition. For therapeutic or prophylactic treatment of a vascular disease or related condition in a mammal in which neutrophils are involved or implicated, a compound of the invention may conveniently be administered by an oral or parenteral route, either alone or simultaneously or sequentially with other therapeutically active agents customarily administered for the condition. The utility of the compound of the invention in such treatment of vascular diseases and related conditions may be demonstrated using the procedures described in International Patent Application, Publication No. WO 92/22309.

The various aspects of the invention will now be illustrated by the following non-limiting examples in which, unless stated otherwise:

(i) temperatures are given in degrees Celsius (°C.); operations were carried out at room or ambient temperature, that is, at a temperature in the range of 18°–25° C.;

(ii) organic solutions were dried over anhydrous magnesium sulfate; evaporation of solvent was carried out using a rotary evaporator under reduced pressure (600–4000 pascals; 4.5–30 mm Hg) with a bath temperature of up to 60° C.;

(iii) chromatography means 'flash chromatography' (method of Still) carried out on Merck Kieselgel (Art 9385 from E. Merck, Darmstadt, Germany), elution using both step and ramp gradients is denoted by the parenthetical term "gradient" followed by the initial and final solvent ratios; thin layer chomatography (TLC) was carried out on silica plates, for example 0.25 mm silica gel GHLF plates (Art 21521 from Analtech, Newark, Del., USA);

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory nuclear magnetic resonance (NMR) spectra; and, where examined, were substantially pure by HPLC;

(vii) yields are given for illustration only and are not necessarily those which may be obtained by diligent process development; preparations were repeated if more material was required;

(viii) when given, NMR data is in the form of delta values for major diagnostic protons, given in parts per million (ppm relative to tetramethylsilane (TMS) as an internal standard, determined at 250 MHz using DMSO-$d_6$ as solvent; conventional abbreviations for signal shape are used; for AB spectra the directly observed shifts are reported;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms;

(xii) mass spectra (MS) were run with an electron energy of 70 electron volts in the chemical ionizaton mode using a direct exposure probe; where indicated ionization was effected by electron impact (EI) or fast atom bombardment (FAB); generally, only peaks which indicate the parent mass are reported; and (xiii) HPLC was used to establish the ratio of SSS:SSR diastereoisomers of formula I in isolated material, using a Hypersil C18, 3 µm, 10 cm×4.6 mm column and a mobile phase of 0.02M tetrabutyl ammonium phosphate/acetonitrile (75:25) at pH 7.5. The flow rate was 1.5 ml/min, the injection volume was 20 µl by valve and the detection wavelength was 254 nm. The retention time for the SSS diastereoisomer is typically 12–13 minutes, and for the SSR diastereoisomer is typically 20–21 minutes. Alternatively a SUPELCO LC-18 reversed-phase, 25 cm×4.6 mm column may be used, with water:acetonitrile (60:40) as eluant, with a flow rate of 1.0 ml/minute.

EXAMPLE 1

A crystalline diastereomeric mixture of SSS diastereoisomer and SSR diastereoisomer (0.67 g), in a ratio of about 85:15 SSS:SSR, was added to toluene (4.5 ml) and heated to 80° C. to give a clear solution. The solution was cooled to 55° C. over 30 minutes and seeded with pure SSS diastereoisomer. The solution was then allowed to cool to 25° C. over one hour and then cooled in an ice bath for a further hour. The crystalline product was collected by filtration, washed with cold toluene (2 ml) and dried at 50° C. This procedure was repeated to give crystalline SSS diastereoisomer of formula I (0.43 g) containing less than 2% SSR diastereoisomer by HPLC analysis; $^{25}[\text{alpha}]_D$ –90° (c=1.50 in ethanol); m.p. 147.5–148.5° C.; NMR ($d_6$-DMSO): 0.92 (m, 12H), 1.75 (m, 1H), 1.81–2.15 (m, 5H), 3.61 (m, 1H), 3.80 (s, 3H), 3.91 (m, 1H), 4.44 (m, 2H), 4.62 (t, 1H), 6.96 (d, 2H), 7.91 (d, 2H), 8.34 (d, 1H), 8.60 (d, 1H); NMR ($d_6$-DMSO/$D_2O$): 0.75 (d,3H), 0.89 (m, 9H), 1.70–2.19 (m, 6H), 3.56 (m, 1H), 3.75 (s, 3H), 3.84 (m, 1H), 3.98 (d, 1H), 4.37 (m, 2H), 6.94 (d, 2H), 7.76 (d, 2H); mass spectrum (chemical ionisation): 500 (M+H); microanalysis, found: C, 57.72; H, 6.62.; N, 8.36%; $C_{24}H_{32}F_3N_3O_5$ requires: C, 57.70; H, 6.45; N, 8.41%.

Using differential scanning calorimetry, this material showed an initial change at about 149.5° C., with a peak at about 151° C.

[A similar result was obtained using a crystalline diastereomeric mixture having an SSS:SSR ratio of 76:24, and recrystallising twice from toluene.

A similar result was also obtained using a mixture of ethyl acetate and hexane as solvent. The crystalline diastereomeric mixture of SSS and SSR diastereoisomers was dissolved in ethyl acetate, the volume reduced by distillation and the hot solution (60° C.) diluted with hexane, maintaining a clear solution. The solution was cooled to 50° C., seeded with pure SSS diastereoisomer and allowed to cool. The proportions of starting material and solvents used were similar to those used in Example 5.]

The crystalline diastereomeric mixture of SSS and SSR diastereoisomers used as starting material was obtained as described in Example 4 or 5 below.

EXAMPLE 2

0.6M Sodium hydroxide solution (260 ml) was added to a solution of (S)-1-[(S)-2-(4-methoxybenzamido)-3-methylbutyryl]-N-[(S)-2-methyl-1-((R)-2,2,2-trifluoro-1-hydroxyethyl)propyl]pyrrolidine-2-carboxamide (25.7 g) in a mixture of t-butanol (205 ml) and water (255 ml) at 0° C. A solution of potassium permanganate (24.2 g) in water (385 ml) was added dropwise with stirring, over one hour and the resultant reaction mixture was stirred for a further hour at 0° C. Methanol (100 ml) was then added and the mixture stirred at 0° C. for a further two hours. The reaction mixture was filtered through diatomaceous earth and the still cooled filtrate was acidified with 1M hydrochloric acid (200 ml), which resulted in the formation of a voluminous white precipitate. Solid sodium chloride was added to the mixture to the point of saturation, followed by diethyl ether (200 ml) and ethyl acetate (200 ml). The mixture was stirred until all the solid had dissolved. The organic phase was separated and the aqueous layer was extracted with diethyl ether:ethyl acetate (1:1). The combined organic phases were washed with brine, dried (MgSO₄), and the solvent removed by evaporation under vacuum. The resultant foam was dissolved in warm toluene (150 ml) and allowed to stand for 16 hours at ambient temperature. The solid which crystallised was collected by filtration, washed with diethyl ether and dried under vacuum at 40° C. for 3 hours to give crystalline SSS diastereoisomer of formula I (16.5 g) containing <0.5% of the SSR diastereoisomer of formula I; m.p. 149°–151° C. (Trituration of the filtrate resulted in the recovery of an additional crop of the SSS diastereoisomer (6.24 g).)

When diethyl ether was used as solvent of crystallisation, instead of toluene, crystalline SSS diastereoisomer of similar purity was obtained as a mixture of anhydrous and hydrated forms (ratio 1:1); m.p. 116° C.; microanalysis, found: C, 56.48; H, 6.49.; N, 8.20%; $C_{24}H_{32}F_3N_3O_5 \cdot 0.5H_2O$ requires: C, 56.68; H, 6.54; N, 8.26%.

The starting aminoalcohol was obtained as follows:

(i) Trifluoroacetic acid (200 ml) was added to a mixture of N-benzyloxycarbonyl-L-valyl-L-proline tert-butyl ester (80.0 g) in methylene chloride ((300 ml) at 0° C. over approximately 30 minutes. After stirring at 0° C. for one hour, the reaction mixture was allowed to rise to ambient temperature and stirred an additional 3 hours. The reaction mixture was then comcentrated under vacuum and reconcentrated four times from toluene to remove residual trifluoroacetic acid. The resulting viscous oil was dried under vacuum for 16 hours. The crude product was purified on by chromatography on silica gel, usimg methylene chloride as eluant, to give N-benzyloxycarbonyl-L-valyl-L-proline (A) (63.6 g) as a pale yellow viscous oil; NMR (d₆-DMSO): 0.92 (2d, 6H), 1.65–2.05 (2m, 4H), 2.25 (m, 1H), 3.60 (m, 1H), 3.80 (m, 1H), 4.05 (dd, 1H), 4.25 (m, 1H), 5.02 (2d, 2H), 7.35 (m, 5H), 7.50 (d, 1H).

(ii) N-methylmorpholine (16.6 ml) was added in one portion to a stirred solution of compound A in tetrahydrofuran (THF; 550 ml) and the solution was cooled to −35° C. Isobutyl chloroformate (18.9 ml) was then added dropwise to the cooled solution. When addition was complete, the reaction mixture was stirred for one hour and then a solution of 2(R),3(S)-3-amino-4-methyl-1,1,1-trifluoro-2-pentanol (24.5 g) in THF (160 ml) was added dropwise over 30 minutes. The reaction mixture was stirred for an additional hour at −35° C. and then allowed to warm to ambient temperature and stirred for 16 hours. The mixture was filtered and the filtrate washed twice with saturated aqueous sodium bicarbonate solution. The aqueous layers were extracted twice with diethyl ether and the combined organic layers washed with brine and dried. Solvent was removed by evaporation and the crude product was purified by silica chromatography using methylene chloride:toluene (9:1) as eluant, to give (S)-1-[(S)-2-(benzyloxycarbonylamino)-3-methylbutyryl]-N-[(S)-2-methyl-1-[(R)-2,2,2-trifluoro-1-hydroxyethyl)propyl]pyrrolidine-2-carboxamide (55.1 g) (B) as a colourless foam; NMR (300 MHz, d₆-DMSO): 0.90 (9m, 12H), 1.63–2.03 (m, 5H), 3.55 (m, 1H), 3.75 (m, 2H), 4.07 (m, 2H), 4.45 (m, 1H), 5.02 (2d, 2H), 7.35 (m, 5H), 7.45 (d, 1H), 7.65 (d, 1H).

(iii) A solution of compound B (55 g) in ethanol (300 ml) was hydrogenated for 3 hours over 10% palladium on carbon catalyst (5.5 g), under a hydrogen pressure of 55 psi. The reaction mixture was filtered through diatomaceous earth and the filtrate was concentrated under vacuum to give a viscous oil. The oil was triturated with diethyl ether (250 ml) for 16 hours and the resulting solid was collected by filtration to give (S)-1-[(S)-2-amino-3-methylbutyryl]-N-[(S)-2-methyl-1-((R)-2,2,2-trifluoro-1-hydroxyethyl)propyl] pyrrolidine-2-carboxamide (C) (25.6 g) as a white solid; NMR (300 MHz, d₆-DMSO): 0.75–0.97 (m, 12H), 1.42 (s, 1H), 1.65–2.0 (m, 5H), 2.78, 3.20 (each d, total 1H), 3.45, 3.60 (each m, total 1H), 3.82 (m, 1H), 4.10 (m, 1H), 4.45, 4.57 (each m,total 1H), 6.45 (br d, 1H), 7.45, 7.60 (each d, total 1H).

(iv) Compound C was suspended in THF (350 ml) and powdered sodium carbonate (18.5 g) was added. The mixture was cooled to −5° C. and a solution of anisoyl chloride (11.9 g) in THF (50 ml) was added with stirring. The reaction mixture was stirred an additional 2 hours at 0° C. and then allowed to rise to ambient temperature. The reaction mixture was filtered and the filtrate acidified with 1M hydrochloric acid solution (20 ml) and washed with water. The aqueous layer was extracted with twice with diethyl ether and the combined organic layers washed with 50% saturated sodium bicarbonate solution, brine and dried. Solvent was removed by evaporation to give a colourless foam. The foam was triturated with diethyl ether and the resulting solid was collected by filtration and dried under vacuum at 40° C. for 3 hours to give (S)-1-[(S)-2-(4-methoxybenzamido)-3-methylbutyryl]-N-[(S)-2-methyl-1-((R)-2,2,2-trifluoro-1-hydroxyethyl)propyl]pyrrolidine-2-carboxamide as a white solid, m.p. 168°–170° C.; NMR (300 MHz, d₆-DMSO): 0.82–1.05 (m, 12H), 1.65–2.05 (3m, 5H), 2.05–2.25 (m, 1H), 3.60 (m, 1H), 3.82 (s, 3H+t, 1H), 3.93 (m, 1H), 4.12 (m, 1H), 4.45 (m, 2H), 6.45 (d, 1H), 6.98 (d, 2H), 7.65 (d, 1H), 7.90 (d, 2H), 8.35 (d, 1H).

2(R),3(S)-3-Amino-4-methyl-1,1,1-trifluoro-2-pentanol was obtained as follows:

A solution of D-(−)-tartaric acid (50.7 g) in ethanol (200 ml) was added to a solution of 2(RS),3(SR)-3-amino-4-methyl-1,1,1-trifluoro- 2-pentanol (57.8 g) in ethanol (200 ml). The solution was filtered hot and allowed to stand for 16 hours at ambient temperature. The white solid which separated was collected by filtration and washed with a small volume of cold ethanol. The solid was dried under vacuum and recrystallised three times from hot ethanol to give 2(R),3(S)-3-amino-4-methyl-1,1,1-trifluoro-2-pentanol D-(−)-tartaric acid salt (8.3 g); m.p. 135°–137° C.

Alternatively the following procedure may be used:

(i) Triphosgene (23 g) was added in one portion to a well stirred mixture of 2(RS),3(SR)-3-amino-4-methyl-1,1,1-trifluoro-2-pentanol hemioxalate salt (50 g) in toluene (250 ml) and 2M sodium hydroxide solution (350 ml). The reaction began to exotherm and was placed in an ice bath. After 0.5 hour the reaction was warmed to 25° C. and TLC indicated a substantial amount of unreacted amine present. The pH of the solution was readjusted to about 12 using 50% sodium hydroxide solution. An additional portion of triphosgene (8 g) was added and the solution was stirred for 1 hour. The pH of the reaction mixture was lowered to pH 7 using 1M hydrochloric acid and extracted twice with ether. The combined ether layers were washed with water, brine and dried (MgSO₄). The solvent was removed by evaporation to give an oil, which crystallized upon standing. The resulting solid was collected by filtration and washed with ether:hexane (1:1) to give 27 g of 4(RS), 5(SR)-4-isopropyl-5-trifluoromethyl-2-oxazolidinone as a white solid, m.p. 71°–72° C.; $^1$H NMR (300 MHz, DMSO): 8.45 (s, 1H), 5.11 (m, 1H), 3.61 (m, 1H), 1.72 (m, 1H), 0.86 (d, 6H).

(ii) n-Butyllithium (20 ml of a 10M solution in hexane) was added to a solution of 4(RS), 5(SR)-4-isopropyl-5-trifluoromethyl-2-oxazolidinone (35.8 g) in THF (600 ml) at −78° C., followed by stirring for 0.5 hours. (−)-Menthyl chloroformate (41 ml, freshly distilled) was added followed by continuation of stirring at −78° C. for 0.5 hours. The solution was warmed to 25° C. and the reaction quenched by addition of saturated aqueous sodium bicarbonate solution. The product was extracted into ether and washed with water and brine. The solution was dried (MgSO$_4$) and the solvent removed under vacuum. The resulting oil crystallized upon standing to give a solid which was collected by filtration. The solid was washed with ether:hexane (1:1) and dried to give 4(S),5(R)-4-isopropyl-3-[1(R),2(S),5(R)-menthyloxycarbonyl]-5-trifluoromethyl-2-oxazolidinone (23.15 g); m.p. 138°–140° C.; $^1$H NMR (300 MHz, DMSO): 5.51 (dd, 1H), 4.68 (m, 1H), 4.26 (m, 1H), 2.27 (m, 1H), 1.94 (d, 1H), 1.78 (m, 1H), 1.62 (d, 2H), 1.42 (m, 2H), 1.01 (dd, 2H), 0.95–0.84 (m, 24H), 0.71 (d, 3H); $^{19}$FNMR (376.5 MHz, DMSO): −76.9910; 99% d.e. (A further crop of 4.3 g (99% d.e.) was obtained from the mother liquor). [Note: the 4(R),5(S) isomer has m.p. 80°–82° C. and 19FNMR (376.5 MHz, DMSO): −77.0019.

(iii) A solution of 4(S),5(R)-4-isopropyl-3-[1(R),2(S),5(R)-menthyloxycarbonyl]-5-trifluoromethyl-2-oxazolidinone (27 g) in dioxane (70 ml) and 50% potassium hydroxide solution (80 ml) was heated at 100° C. for 2 days. The reaction was cooled, diluted with ether (400 ml) and the organic layer separated. The pH of the aqueous solution was adjusted to 9 (originally about 14) using 6M hydrochloric acid. The aqueous layer was extracted 3 times with ether (300 ml). The organic phases were combined, dried (MgSO$_4$), and added to a well stirred solution of oxalic acid dihydrate (4.5 g) in acetonitrile (100 ml). The solid which precipitated was collected by filtration, washed with ether, and dried under vacuum (60° C.) to give 15.9 g of white solid. The solid was triturated with ether (300 ml), collected by filtration and dried to give 2(R),3(S)-3-amino-4-methyl-1,1,1-trifluoro-2-pentanol hemioxalate salt (13.4 g, 88% yield) as a white solid, m.p. 184°–186° C.; $^1$H NMR (300 MHz, DMSO): 5.71 (bs, 3H), 4.08 (ddd, 1H), 2.88 (m, 1H), 1.81 (m, 1H), 0.92 (m, 6H); Analysis for C$_6$H$_{12}$F$_3$NO.0.5C$_2$H$_2$O$_4$: C, 38.89; H, 6.06; N, 6.48; Found: C, 38.75; H, 5.95; N, 6.47.

EXAMPLE 3

A non-crystalline (amorphous) diastereomeric mixture (foam or oil) of SSS and SSR diastereoisomers of formula I (0.5 g) in a ratio of about 1:1 was dissolved in diethyl ether (2.5 ml), seeded with a crystal of substantially pure SSS diastereoisomer, and allowed to stand for 16 hours. The solid which crystallised was collected by filtration, washed with diethyl ether and allowed to dry to give crystalline SSS diastereoisomer containing SSR diastereoisomer, in 30–45% yield, (ratio SSS:SSR 88:12; anhydrous form:hydrated form 1:1). (A similar result was obtained when a non-crystalline diastereomeric mixture of SSS:SSR 3:2 was used.)

EXAMPLE 4

A non-crystalline diastereomeric mixture of SSS and SSR diastereoisomers of formula I (ratio SSS:SSR 48.5:51.5; 5.18 g) was dissolved in tert-butyl methyl ether (23 ml) and N-methylmorpholine (1.3 ml) was added. The mixture was heated to reflux and a mixture of hydrocarbons having a boiling point of 100°–120° C. (ESSOCHEM 30; 60 ml) was added slowly while maintaining the temperature of the reaction mixture at 98° C. After 25 ml of distillate was collected, the temperature was lowered to 70° C. and a few seed crystals of substantially pure SSS-diastereoisomer were added. The reaction mixture was stirred at 70° C. for one hour, at 60° C. for a further hour, and finally at ambient temperature for 16 hours. The resulting crystalline solid was collected by filtration, washed with ESSOCHEM 30 and allowed to dry to give a crystalline mixture of SSS and SSR diastereoisomers (4.8 g), having a ratio of SSS:SSR of 76:24. This material was added to water (17 ml) with stirring and 2M hydrochloric acid (2 ml) was added. After stirring at ambient temperature for 90 minutes, the crystalline solid was collected by filtration, washed with water and dried (3.88 g). (This was shown by HPLC to have the same SSS:SSR ratio.)

Using a similar procedure but cooling the solution to 65° C. before adding the seed crystals of substantially pure SSS-diastereoisomer and allowing to stir at 65° C., then cooling in ten degree steps holding for one hour at each temperature and finally stirring at ambient temperature for 16 hours, a crystalline mixture of SSS and SSR diastereoisomers of formula I (SSS:SSR ratio of 85:15) was obtained in approximately 85% yield.

EXAMPLE 5

A non-crystalline (amorphous) diastereomeric mixture of SSS and SSR diastereoisomers of formula I (29.4 g) in ethyl acetate (200 ml) was distilled at atmospheric pressure to remove 100 ml of distillate. Further ethyl acetate (166 ml) was then added and the solution again distilled at atmospheric pressure to remove 166 ml of distillate. This procedure was then repeated. The solution was then cooled to 60° C. and hexane (166 ml) was added over 30 minutes at 60° C. to give a clear solution. The solution was cooled to 50° C., seeded with substantially pure crystalline SSS diastereoisomer (0.1 g) and allowed to cool to ambient temperature for 18 hours. The mixture was stirred for a further 18 hours at 0° C., warmed to 20° C. and further hexane (33 ml) added over ten minutes. After stirring for 3 hours at ambient temperature further hexane (50 ml was added) and the mixture stirred for a further 18 hours at ambient temperature. The crystalline product was collected by filtration and dried under vacuum for four hours to give a crystalline mixture of SSS and SSR diastereoisomers (39% yield) having a ratio of SSS:SSR of 85:15 by HPLC.

[Using a similar procedure, but adding N-methylmorpholine (0.8 ml) to the ethyl acetate prior to (or after) distillation and washing the filtered crystalline product with dilute hydrochloric acid and then water (prior to drying under vacuum), gave a crystalline mixture of SSS and SSR diastereoisomers, with similar SSS:SSR ratio, in 60% yield.]

EXAMPLE 6

A crystalline mixture of SSS and SSR diastereoisomers in a ratio of SSS:SSR of about 85:15 (10 g), obtained using the procedure of Example 5, was slurried in acetone (15 ml) and warmed to 40° C. Water (10 ml) was added and the mixture was heated to 55°–60° C. for 90 minutes. The cloudy solution was cooled to 35°–40° C. and further water (5 ml) was added. The mixture was allowed to cool to ambient temperature and stirred for 16 hours. The crystalline solid was collected by filtration and the procedure repeated. The resultant crystalline solid was dried at 40° C. under vacuum to give crystalline SSS diastereoisomer (containing less than 2% SSR diastereoisomer) in a hydrated form with a water content of 6.69% (in 75% yield). A DSC thermogram of this crystalline material (heating rate 2° C./minute) shows an endothermic event with onset at about 91°–92° C., followed by an exothermic event with onset at about 109°–110° C., followed by a further endothermic event at about 148°–149° C. This data, along with TGA data and $^{19}$F NMR spectral data, indicates this crystalline form to be substantially the monohydrate of the gem-diol (of Formula Ib), which has a theoretical (calculated) water content of 6.73%.

A non-crystalline diastereomeric mixture of SSS and SSR diastereoisomers, used as starting material in Examples 3, 4 and 5, was obtained using Procedure 1 or 2 as follows:

Procedure 1

(i) A solution of N-benzyloxycarbonyl-L-valyl-L-proline tert-butyl ester (20 g) in methanol (300 ml) was hydrogenated at 50 psi over 10% palladium on carbon catalyst (2 g) for 12 hours. The reaction mixture was then filtered through diatomaceous earth and the filter cake washed with methanol. The filtrate was evaporated to give L-valyl-L-proline tert-butyl ester (A) (12 g) as an oil; NMR (300 MHz, $d_6$-DMSO): 0.80 (d, 3H), 0.92 (d, 3H), 1.74 (s, 9H), 1.79–2.15 (m, 5H), 3.22 (d, 1H), 3.30 (bs, 2H), 3.40 (m, 1H), 3.62 (m, 1H), 4.16 (dd, 1H).

(ii) The ester (A) (12.5 g) was dissolved in tetrahydrofuran (THF; 100 ml) and cooled to 0° C. A solution of anisoyl chloride (8.37 g) in THF (200 ml) was added with stirring, followed by triethylamine (18 ml). After one hour, volatile material was removed by evaporation. The resulting material was diluted with ethyl acetate and washed sequentially with water, saturated ammonium chloride solution, saturated sodium bicarbonate solution and brine. The organic solution was dried ($Na_2SO_4$) and solvent removed by evaporation. The resulting material was purified by silica chromatography, using methanol:methylene chloride (3:97) as eluant, to give N-(4-methoxybenzoyl)-L-valyl-L-proline tert-butyl ester (B) as a foam; NMR (300 MHz, $d_6$-DMSO): 0.94 (d, 3H), 0.99 (d, 3H), 1.30 (s, 9H), 1.76 (m, 1H), 1.80 (m, 2H), 2.13 (m, 2H), 3.61 (m, 1H), 3.80 (s,3H), 3.93 (m, 1H), 4.17 (dd, 1H), 4.46 (t, 1H), 6.96 (d, 2H), 7.90 (d, 2H), 8.35 (d, 1H).

(iii) The ester (B) (7.13 g) was dissolved in trifluoroacetic acid (85 ml) and the resulting solution allowed to stir for 30 minutes. Volatile material was removed by evaporation and the residue dissolved in ethyl acetate and washed with water. The organic layer was dried ($Na_2SO_4$) and the solvent removed by evaporation. The resulting material was purified by silica chromatography, eluting with methanol:methylene chloride:acetic acid, 97:2:1) to give N-(4-methoxybenzoyl)-L-valyl-L-proline (6.5 g) (C) which was used without further purification; NMR (300 MHz; $d_6$-DMSO): 0.87 (d, 3H), 0.99 (d, 3H), 1.88 (m, 3H), 2.15 (m, 2H), 3.64 (m, 1H), 3.80 (s, 3H), 3.97 (m, 1H), 4.24 (dd, 1H), 4.44 (t, 1H), 6.96 (d, 2H), 7.90 (d, 2H), 8.37 (d, 1H).

(iv) Compound (C) (7.1 g), 2(RS),3(SR)-3-amino-4-methyl-1,1,1-trifluoro-2-pentanol (3.8 g, free base) and N-hydroxybenzotriazole hydrate (5.5 g) were dissolved in dimethylformamide (DMF; 40 ml) and triethylamine (7.1 ml) was added with stirring. 1-(3-Dimethylaminopropyl)-3-ethylcarbodiimide (5.9 g) was then added and the resulting mixture was allowed to stir for 12 hours. The reaction mixture was diluted with ethyl acetate and washed with 1M hydrochloric acid (twice), water, 1M sodium hydroxide solution and brine. The organic solution was dried and the solvent was removed by evaporation. The resulting material was purified by silica chromatography (gradient elution, ethyl acetate:methylene chloride (30:70) to methanol:methylene chloride (5:95)) to give (S)-1-[(S)-2-(4-methoxybenzamido)-3-methylbutyryl]-N-[2-methyl-1-(2,2,2-trifluoro-1-hydroxyethyl)propyl]pyrrolidine-2-carboxamide (6.6 g) (D) as a white foam; NMR ($d_6$-DMSO): 0.93 (m, 12H), 1.73–2.15 (m, 6H), 3.62 (m, 1H), 3.76 (m, 3H), 4.10 (m, 1H), 4.42 (m, 2H), 6.41 (d, 1H), 6.57 (d, 1H), 6.98 (d, 2H), 7.24 (d, 1H), 7.61 (d, 1H), 7.87 (d, 2H), 8.33 (t, 1H).

(v) 0.6M Sodium hydroxide solution (10 ml) was added to a solution of the aminoalcohol (D) (1.0 g) in tert-butyl alcohol (8 ml) and water (10 ml) and the mixture cooled to 5° C. A solution of potassium permanganate (1.0 g) in water (20 ml) was then added while maintaining the temperature below 10° C. After 2 hours, methanol (4 ml) was added and the reaction mixture stirred until the purple colour had disappeared. The reaction mixture was then filtered through diatomaceous earth and solid sodium chloride (11 g) was added to the filtrate. The mixture was extracted with tert-butyl methyl ether and the aqueous phase washed with a mixture of tert-butyl methyl ether and methyl ethyl ketone. The combined organic extracts were washed with saturated sodium bicarbonate solution, 0.5M hydrochloric acid, water and then dried. Solvent was removed by evaporation to give a diastereomeric mixture of SSS and SSR diastereoisomers of formula I as a foam (SSS:SSR ratio of 3:2).

Alternatively, step (v) was carried out as follows:

1-(3-Dimethylaminopropyl)-3-ethylcarbodiimide (12.6 g), followed by dichloroacetic acid (2.2 ml) was added to a cold solution of (S)-1-[(S)-2-(4-methoxybenzamido)-3-methylbutyryl]-N-[2-methyl-1-(2,2,2-trifluoro-1-hydroxyethyl)propyl]pyrrolidine-2-carboxamide (6.6 g) in DMSO (30 ml) and toluene (30 ml). The reaction was allowed to warm to ambient temperature and stirred for a total of 2.5 hours. The reaction mixture was poured into ethyl acetate and washed with 1M hydrochloric acid solution, saturated sodium bicarbonate, and brine. The solution was dried ($MgSO_4$) and the solvent removed by evaporation to give a mixture of SSS and SSR diastereoisomers of formula I as an oil.

Procedure 2

(1) N-methylmorpholine (46 ml) was added to a mixture of L-valyl-L-proline hydrochloride (34 g) in THF (850 ml), followed by trimethylchlorosilane (41 ml) maintaining the temperature below 30° C. The mixture was stirred for 2 hours and then cooled to 0° C. Further N-methylmorpholine (16.5 ml) was added, followed by a solution of 4-anisoyl chloride (18 ml) in THF (25 ml), maintaining the temperature below 5° C. After 15 minutes, the mixture was filtered and the filtrate concentrated in vacuo to a yellow oil. The oil was dissolved in ethyl acetate (100 ml) and basified to pH 7–8 with saturated potassium bicarbonate solution (100 ml). The aqueous layer was separated and washed with ethyl acetate (50 ml). The aqueous layer was then acidified to pH 2–3 with 2M hydrochloric acid solution and extracted with ethyl acetate (150 ml). The organic extract was concentrated under vacuum and toluene (150 ml) was added. The solution was again concentrated under vacuum until about 50 ml of toluene was collected. The solution was then added dropwise to hexane (400 ml) with stirring to give a white solid, which was filtered, washed with hexane and dried under vacuum to give N-(4-methoxybenzoyl)-L-valyl-L-proline (40 g), having a similar NMR to that given in Procedure 1, step (iii) above.

(ii) N-methylmorpholine (36.8 ml) was added to a solution of N-(4-methoxybenzoyl)-L-valyl-L-proline (34.8 g) in THF (100 ml) and methyl tert-butyl ether (150 ml) and the mixture was cooled to −5° C. A solution of isobutylchloroformate (14.4 ml) in methyl tert-butyl ether (30 ml) was added over 30 minutes, maintaining the temperature at −5° C. during the addition. The reaction mixture was stirred at −5° C. for a further 30 minutes and then 2(RS),3(SR)-3-amino-4-methyl-1,1,1-trifluoro-2-pentanol oxalate salt (22.3 g) was added and the temperature of the mixture allowed to rise to 20° C. over one hour. Water (100 ml) and sodium bicarbonate (5 g) were added and the mixture stirred for 10 minutes. The organic phase was separated, washed with 2M hydrochloric acid solution (50 ml), brine, and evaporated under reduced pressure at a temperature below 50° C. to give (S)-1-[(S)-2-(4-methoxybenzamido)-3-methylbutyryl]-N-[2-methyl-1-(2,2,2-trifluoro-1-hydroxyethyl)propyl] pyrrolidine-2-carboxamide (42 g) as a foam, having a similar NMR to that given in Procedure 1, step (iv) above.

(iii) tert-Butanol (60 ml), water (360 ml) and 48% w/w sodium hydroxide solution (13.9 ml) was added to a solution of (S)-1-[(S)-2-(4-methoxybenzamido)-3-methylbutyryl]-N-[2-methyl-1-(2,2,2-trifluoro-1-hydroxyethyl)propyl]-pyrrolidine-2-carboxamide (42 g) in tert-butanol (340 ml). The solution was cooled to 5° C. and a solution of potassium permanganate (40.1 g) in water (750 ml) was added over one hour at 5°–10° C. The reaction mixture was stirred for a further hour at this temperature and then methanol (100 ml) was added and the mixture stirred for 2 hours at 5°–10° C. The reaction mixture was filtered through diatomaceous earth and the filter cake washed with water (60 ml). Sodium chloride (400 g) and methyl tert-butyl ether (200 ml) was added to the filtrate, the mixture stirred for 10 minutes and the organic phase separated. The aqueous phase was extracted with methyl tert-butyl ether (50 ml) and the combined organic phases washed successively with 2M hydrochloric acid, water, sodium bicarbonate solution and brine. The organic solution was dried (MgSO$_4$) and volatile material was removed by evaporation to give a diastereomeric mixture of SSS and SSR diastereoisomers of formula I as a foam (SSS:SSR ratio of about 1:1).

2(RS),3(SR)-3-Amino-4-methyl-1,1,1-trifluoro-2-pentanol, used in Procedure 1, step (iv) and in Procedure 2, step (ii), may be obtained as described in U.S. Pat. No. 4,910,190 or 3-amino-4-methyl-1,1,1-trifluoro-2-pentanol (as a mixture of diastereoisomers which may be used instead) was obtained as follows:

(i) A solution of urea (72 g) in DMF (810 ml) was added to sodium nitrite (90 g), stirred for 10 minutes and then cooled to 15° C. Isobutyl iodide (97.2 ml) was added over 30 minutes and the reaction mixture allowed to stir at ambient temperature for 20 hours. The mixture was re-cooled to 15° C. and water (810 ml) was added slowly. The mixture was was stirred for 5 minutes at ambient temperature and then extracted twice with methyl tert-butyl ether. The combined organic extracts were washed twice with 20% aqueous sodium thiosulphate solution and concentrated under vacuum to give 2-methyl-1-nitropropane (39 g), which was used without further purification.

(ii) 3A Molecular sieves (27.04 g) were heated at 120° C. under vacuum for 20 hours and added to a solution of 2-methyl-1-nitropropane (13.0 g) in methyl tert-butyl ether (420 ml). The mixture was stirred for 5 minutes, potassium carbonate (64.5 g) added and the mixture stirred a further 30 minutes. The mixture was cooled to 15° C. and fluoral hydrate (22.0 g) was added over 30 minutes. The reaction mixture was stirred at ambient temperature for 16 hours, then cooled to 15° C. and water (270 ml) added. After stirring for 5 minutes at ambient temperature, the organic phase was separated and washed with 10% aqueous potassium carbonate, 2M hydrochloric acid solution and water. Solvent was then removed by evaporation under reduced pressure at a temperature below 40° C. and the oil azeotroped dry with isopropyl alcohol at a temperature below 50° C. to give 4-methyl-3-nitro-1,1,1-trifluoro-2-pentanol (21.3 g) as an oil which was used without further purification.

(iii) A solution of 4-methyl-3-nitro-1,1,1-trifluoro-2-pentanol (17.1 g) in isopropanol (115 ml) and acetic acid (0.43 ml) was hydrogenated over 10% palladium on carbon (2.4 g) at 3.5 barg pressure until uptake of hydrogen was complete. The catalyst was removed by filtration through diatomaceous earth and the filter cake washed with isopropanol. The filtrate was evaporated under vacuum until no further isopropanol distilled and the residue dissolved in acetonitrile (40 ml). A solution of oxalic acid (3.94 g) in acetonitrile (80 ml) was added with stirring and the mixture cooled to 5° C. The product which crystallised was collected by filtration, washed with cold acetonitrile and dried at 50° C. to give 3-amino-4-methyl-1,1,1-trifluoro-2-pentanol as its oxalate salt (9.08 g).

Scheme 1

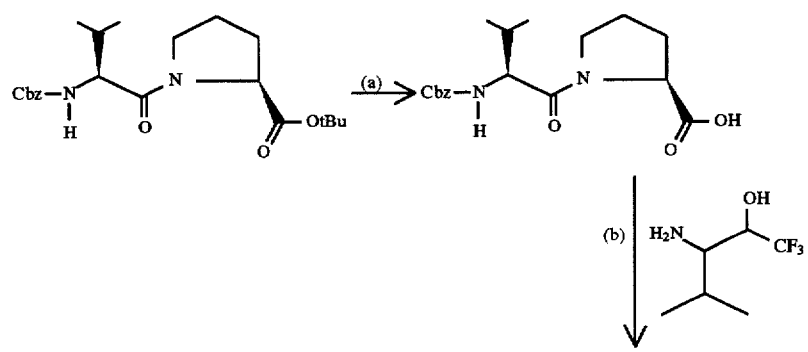

-continued
Scheme 1

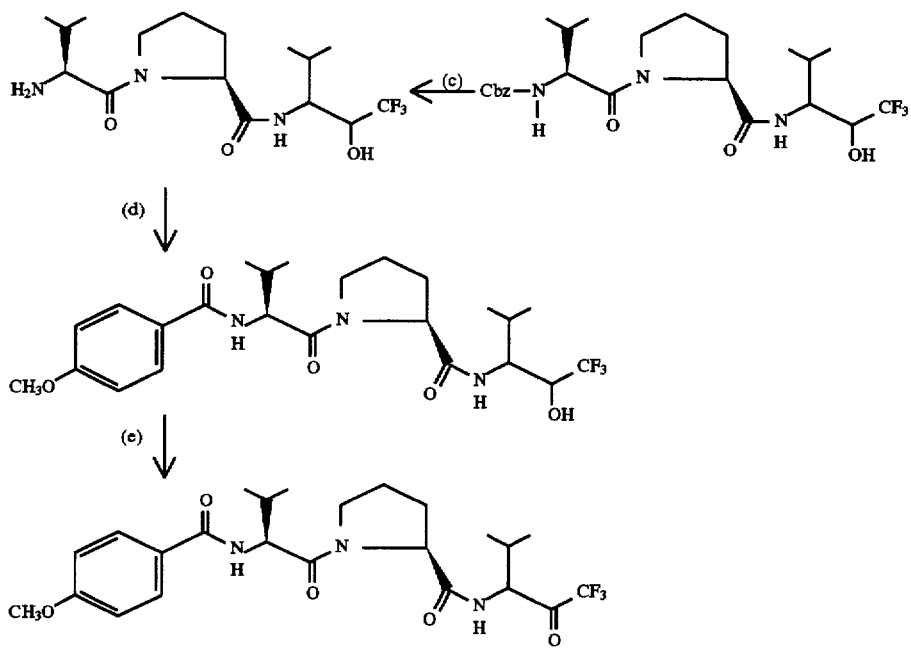

amorphous, diastereomeric mixture
of SSS and SSR diastereoisomers
Cbz = benzyloxycargbonyl
Suitable reagents include:
(a) trifluoroacetic acid
(b) isobutyl chloroformate, N-methylmorpholine, THF
(c) hydrogen, 10% palladium on carbon, ethanol
(d) anisoyl chloride, sodium carbonate, THF
(e) $KMnO_4$, NaOH, tert-butanol, water or 1-(3-dimethylaminopropyl)-3-ethylcarbodiimide, $Cl_2CH.CO_2H$, DMSO, toluene Scheme 2

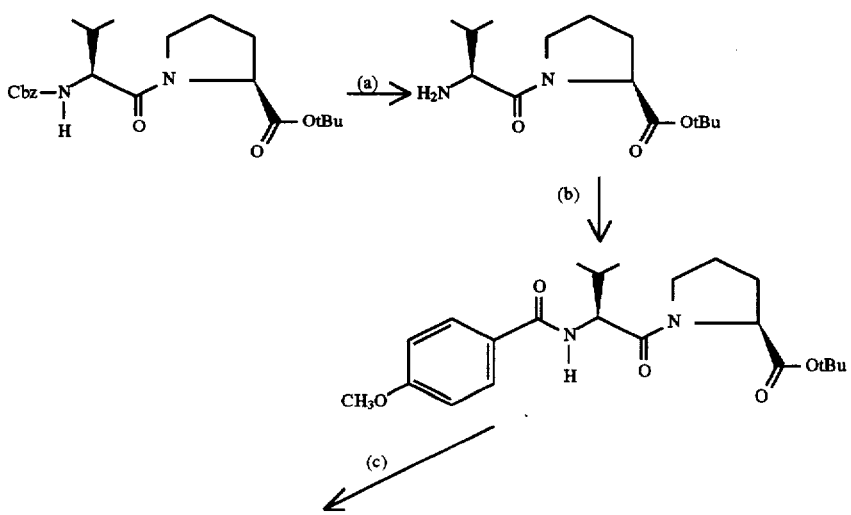

-continued
Scheme 2

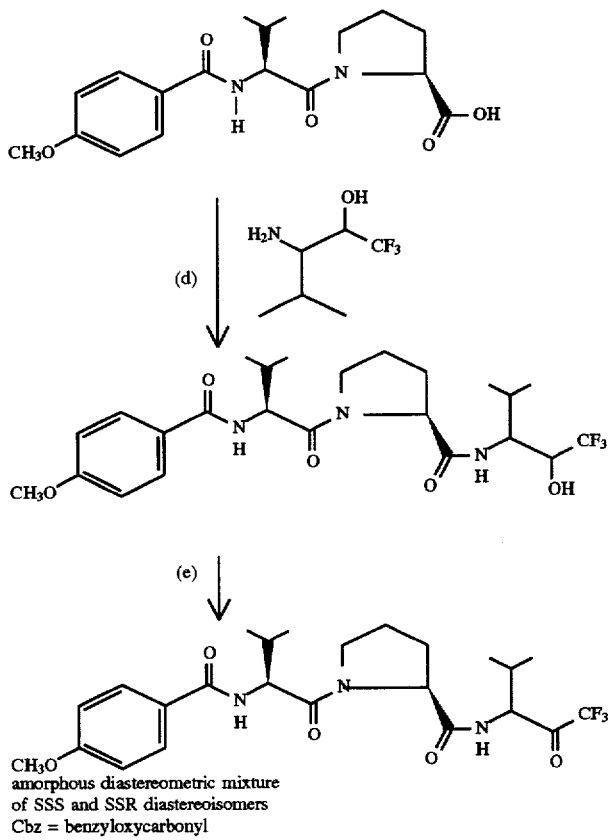

amorphous diastereometric mixture
of SSS and SSR diastereoisomers
Cbz = benzyloxycarbonyl

What is claimed is:
1. A crystalline form of the compound of formula I

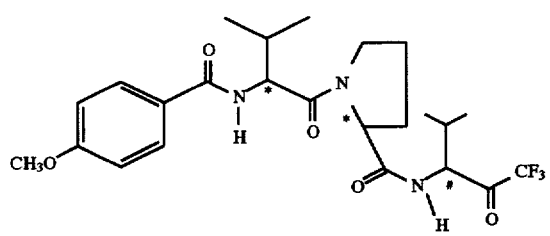

which has a content of 75% or more of the diastereoisomer having the S configuration at the chiral centres marked * and #, or a crystalline solvated form thereof.

2. A crystalline form as claimed in claim 1, or a crystalline solvate thereof, which has a content of 95% or more of the diastereoisomer having the S configuration at the chiral centres marked * and #, or a crystalline solvated form thereof.

3. A crystalline form as claimed in claim 1 which has a content of 95% or more of the diastereoisomer having the S configuration at the chiral centers marked * and # or a crystalline solvated form which is a crystalline hydrated form.

4. A crystalline solvated form as claimed in claim 1, which is a compound of the formula Ib

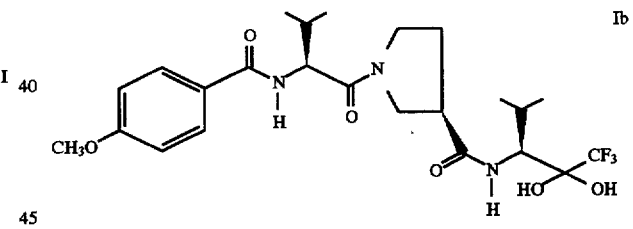

or a hydrated form thereof, or a crystalline pharmaceutically-acceptable salt thereof.

5. A crystalline form as claimed in claim 1, which has a content of 95% or more of the diastereoisomer having the S configuration at the chiral centers marked * and # and which has an X-ray powder diffraction pattern with specific peaks at 2-theta=8.95, 11.17, 11.47, 13.86, 15.49, 17.86, 18.22, 19.24, 21.58 and 21.92°.

6. A crystalline solvated form as claimed in claim 1, which is a hydrated form having an X-ray powder diffraction pattern with specific peaks at 2-theta=6.62, 10.43, 13.30, 16.17, 19.51, 21.37 and 22.80°.

7. A crystalline solvated form as claimed in claim 1, which is a hydrated form having an X-ray powder diffraction pattern with specific peaks at 2-theta=6.20, 9.81, 10.29, 12.33, 12.44, 14.22 and 17.92°.

8. A crystalline form as claimed in claim 1 which has an infra-red spectrum, obtained by the solvent cast technique from acetonitrile castings onto a salt window, having sharp peaks at 2968, 1761, 1629, 1607, 1533, 1503, 1443, 1259, 1209, 1178, 1158, 1032, 845 and 767 $cm^{-1}$.

9. A crystalline form as claimed in claim 1 having a melting point in the range 147°–151° C.

10. A crystalline form as claimed in claim 1, having an endothermic event determined by differential scanning calorimetry with a heating rate of 2° C. per minute at about 91°–92° C., followed by an exothermic event with onset at about 109°–110° C., followed by an endothermic event with onset at about 148°–149° C.

11. A crystalline form as claimed in claim 1 having a melting point 116°–117° C.

12. A pharmaceutical composition comprising a crystalline form as claimed in any preceding claim, together with a pharmaceutically acceptable diluent or carrier.

13. A process for the manufacture of a crystalline form or solvated form as claimed in claim 1 which comprises forming crystals from a solution of a non-crystalline mixture of SSS and SSR diastereoisomers of formula I, or solvate thereof, wherein the ratio of said SSS diastereoisomer to said SSR diastereoisomer in said non-crystalline mixture is about 1:1 to about 3:2, in a solvent selected from diethyl ether, di-n-propyl ether and di-n-butyl ether or in a solvent which is a mixture of methyl tert-butyl ether and hexane or a mixture of ethyl acetate and hexane, optionally in the presence of a catalytic amount of a tertiary base.

14. A process as claimed in claim 13 modified by starting with a solution of a non-crystalline mixture of the SSS and SSR diastereoisomers, or solvate thereof, in a solvent having a lower boiling point than ethyl acetate, adding ethyl acetate to the solution and concentrating the solution by evaporation or distillation, prior to adding hexane.

15. A process for the manufacture of a crystalline form or solvated form of the compound of formula I as claimed in claim 1 which comprises heating a non-crystalline mixture of SSS and SSR diastereoisomers of formula I, or solvate thereof, wherein the ratio of said SSS diastereoisomer to said SSR diastereoisomers in said non-crystalline mixture is about 1:1 to about 3:2, with a base selected from an N-(1–4)alkylmorpholine, an N-(1–4C)alkylpiperidine, pyridine and pentaisopropylguanidine, in a solvent selected from methyl tert-butyl ether, hexane or a mixture of hydrocarbons having a boiling point in the range 100°–120° C., or a mixture thereof, or a mixture of ethyl acetate and hexane, seeding the solution and allowing the solution to cool.

16. A process for the manufacture of a crystalline form of formula I

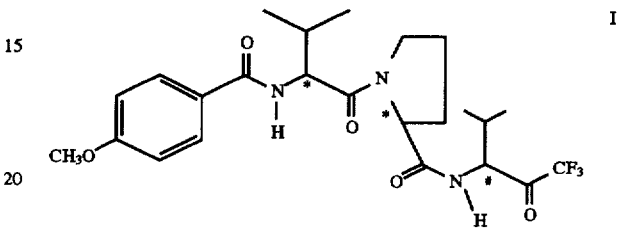

which has a content of 95% or more of the diastereoisomer having the S configuration at the chiral centers marked * and #, or crystalline solvated form thereof comprising recrystallisation one or more times of the product obtained from the process of claim 13, 14 or 15 using a solvent selected from toluene, a mixture of ethyl acetate and hexane, a mixture of acetone and water, and a mixture of tert-butanol and water.

* * * * *

UNITED STATES PATENT AND TRADEMARK OFFICE
CERTIFICATE OF CORRECTION

PATENT NO. : 5,739,157  Page 1 of 3

DATED : April 14, 1998

INVENTOR(S) : Pegg et al.

It is certified that error appears in the above-identified patent and that said Letters Patent is hereby corrected as shown below:

In The Specification:

Column 2, line 40, the following formula:
"
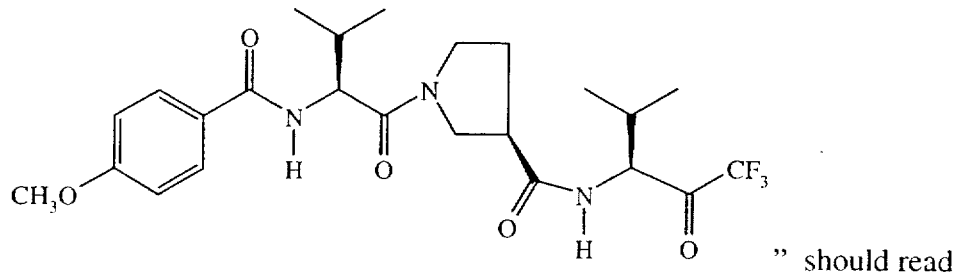
" should read

--
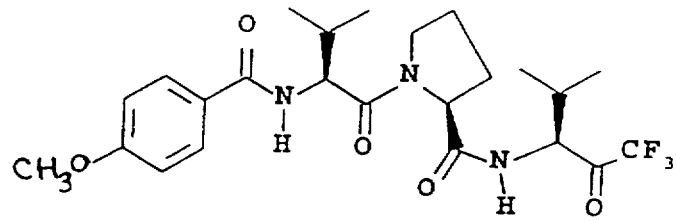
--.

UNITED STATES PATENT AND TRADEMARK OFFICE
CERTIFICATE OF CORRECTION

PATENT NO. : 5,739,157

DATED : April 14, 1998

INVENTOR(S) : Pegg et al.

It is certified that error appears in the above-identified patent and that said Letters Patent is hereby corrected as shown below:

In The Specification:

Column 3, line 1, the following formula:
"
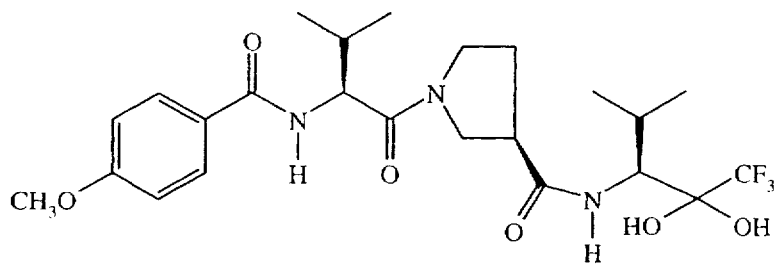
" should read

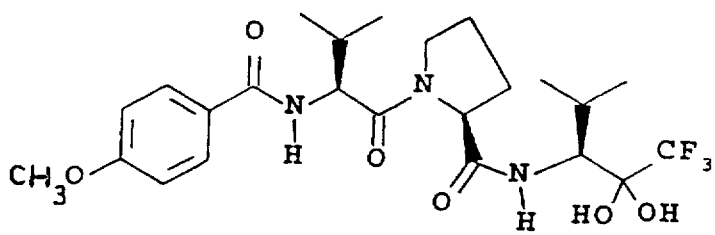
--.

UNITED STATES PATENT AND TRADEMARK OFFICE
CERTIFICATE OF CORRECTION

PATENT NO. : 5,739,157
DATED : April 14, 1998
INVENTOR(S) : Pegg et al.

It is certified that error appears in the above-identified patent and that said Letters Patent is hereby corrected as shown below:

In the Claims:

Claim 4, line 40, the following formula:
"
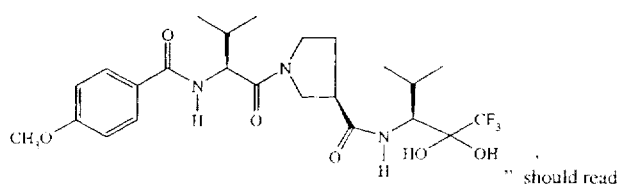
" should read

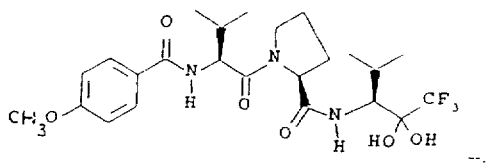
--.

Signed and Sealed this

Seventh Day of September, 1999

Attest:

Q. TODD DICKINSON

Attesting Officer    Acting Commissioner of Patents and Trademarks